United States Patent [19]

Ichimori et al.

[11] Patent Number: 5,437,995
[45] Date of Patent: Aug. 1, 1995

[54] MONOCLONAL ANTIBODY AGAINST AN ACIDIC FGF PROTEIN AND HYBRIDOMA FOR ITS PRODUCTION

[75] Inventors: Yuzo Ichimori, Osaka; Koichi Kondo; Koichi Igarashi, both of Kyoto; Masaharu Sendo, Osaka, all of Japan

[73] Assignee: Takeda Chemical Industries, Ltd., Osaka, Japan

[21] Appl. No.: 26,257

[22] Filed: Mar. 4, 1993

Related U.S. Application Data

[63] Continuation of Ser. No. 588,343, Sep. 26, 1990, abandoned.

[30] Foreign Application Priority Data

Sep. 26, 1989 [JP] Japan .................................. 1-251177
Dec. 20, 1989 [JP] Japan .................................. 1-331600

[51] Int. Cl.⁶ ........................ C12N 5/12; C07K 16/22
[52] U.S. Cl. ........................... 435/240.27; 530/388.24
[58] Field of Search ...................... 530/388.23, 388.24; 435/240.27, 172.2, 70.21

[56] References Cited

U.S. PATENT DOCUMENTS 5,187,062  2/1993  Sato et al. ........................... 435/7.94

FOREIGN PATENT DOCUMENTS

WO90/05915  5/1990  WIPO .

OTHER PUBLICATIONS

Ichimori, Y. et al, Biochem Biophys Res Com, 175(1):291–297, Feb. 28, 1991.
Burgess et al., J. Cell Biol, 111:2129–2138, Nov. 1990.
Masogolia, S. L. et al., J Cell Physiol, 132:531–537, 1987.
Riss, et al., Journal of Cellular Physiology, 138:405–414 (1989).
The 27th Meeting: The Radioimmunoassay Research Society of Japan; Nov. 26, 1988–and English Translation.
The 62nd Meeting: The Japanese Endocrine Society, Jun. 1, 1990–and English Translation.

*Primary Examiner*—David L. Lacey
*Assistant Examiner*—Susan A. Loring
*Attorney, Agent, or Firm*—David G. Conlin; David S. Resnick

[57] ABSTRACT

The present invention provides a hybrid cell line producing monoclonal antibody to an acidic fibroblast growth factor (aFGF) protein. The hybridoma is established by fusing spleen cells from immunized mice with myeloma cells. The hybridomas are cultured as clones, and antibodies obtained from the individual clones are tested for their specificity for aFGF protein. Antibodies can be obtained from the culture growth medium or from ascitic fluid of mice bearing the hybridoma tumor. Diagnostic and therapeutic uses of the monoclonal antibody are also disclosed.

2 Claims, 12 Drawing Sheets

```
                    BspMI
         10         20         30         40         50         60
AAGCTTACCT GCCATGTTTA ATCTGCCTCC CGGGAATTAC AAGAAGCCCA AACTCCTCTA 70         80         90        100        110        120
CTGCAGCAAC GGGGGCCACT TCCTGAGGAT TCTTCCGGAT GGCACAGTGG ATGGGACAAG 130        140        150        160        170        180
GGACAGGAGC GACCAGCACA TTCAGCTGCA ACTCAGTGCG GAAAGCGTGG GGGAGGTGTA 190        200        210        220        230        240
TATAAAGAGT ACCGAGACTG GCCAGTACTT GGCAATGGAC ACCGACGGGC TTTTATACGG 250        260        270        280        290        300
CTCACAGACA CCAAATGAGG AATGTTTGTT CCTGGAAAGG CTGGAGGAGA ACCATTACAA 310        320        330        340        350        360
CACCTATATA TCCAAGAAGC ATGCAGAGAA GAATTGGTTT GTTGGCCTCA AGAAGAATGG 370        380        390        400        410        420
GAGCTGCAAA CGCGGGTCCTC GGACTCACTA TGCCAGAAAA GCAATCTTGT TTCTCCCCCT 430        440        450        460        470        480
GCCAGTCTCT TCTGATTAAT AAGGATCCGA ATTC
                              ↑
                            BamHI
```

MONOCLONAL ANTIBODY AGAINST AN ACIDIC FGF PROTEIN AND HYBRIDOMA FOR ITS PRODUCTION

This is a continuation of application Ser. No. 07/588,343 filed on Sep. 26, 1990 now abandoned.

FIELD OF THE INVENTION

The present invention relates to monoclonal antibodies against acidic fibroblast growth factor (also, hereinafter briefly referred to as aFGF) proteins, hybridomas secreting the same, their preparation and use thereof.

BACKGROUND OF THE INVENTION

The aFGF is an acidic polypeptide hormone which is localized in brain, retina, neuron-related tissue, etc. and which has a molecular weight of about 16000. The aFGF exhibits growth promoting action on fibroblasts such as BALB/c 3T3 cells and the like, and on almost all mesoderm-derived cells (D. Gospodarowicz et al.; Endocrine Reviews, 8: 95 (1987)).

This aFGF also has neovascularizing activity. The neovascularizing activity of aFGF co-operative with its cell growth activity suggests the possibility of its use as agents for treating injured lesions and burns and for preventing and/or treating thrombosis, arteriosclerosis, and the like.

The natural type human aFGF is present in an extremely small amount among tissues or cells. Attempts to obtain this factor from human tissues have encountered serious difficulties arising from various limitations. Further, any quantitative assay for easily determining aFGF has not been established to date. Due to such significant difficulties, much fundamental information with regard to, for example, characteristics of aFGF, which are necessary for developing aFGF as a therapeutic agent, has not yet been uncovered.

If various fundamental information with regard to aFGF is obtained, for example, the in vivo distribution of aFGF and the system for its production, the development of aFGF as a drug will be accelerated. The quantitative determination of aFGF is important even upon the purification from recombinant products. Moreover, it is very important to trace aFGF level of blood in animals which are administered with aFGF; however, it is impossible to assay the concentration by the prior methods using 3T3 cells due to the comtamination of serum in a sample.

The determination of aFGF is usually achieved by culturing 3T3 cells under a reduced serum concentration, then adding aFGF to the 3T3 cells arrested in DNA synthesis, and calculating the aFGF concentration from the degree of recovery in DNA synthesizing activity thereby. This method has, however, several drawbacks including, requiring of delicate manipulations, the possibility of large errors in the aFGF determination and since the method requires the use of cells it is time-consuming.

Accordingly, there is a desire in the art for a simple means for the accurate determination of aFGF.

The present inventors made various investigations and studies to discover a practical means for aFGF protein determination. As a result, the inventors succeeded in preparing monoclonal antibodies against aFGF protein and capable of assaying the same. The present inventors have conducted further studies on the basis of this achievement and now developed the present invention.

SUMMARY OF THE INVENTION

The present invention relates to
(1) a monoclonal antibody which recognizes an acidic fibroblast growth factor protein and has the following characteristics:
 (a) molecular weight; about 140000 to about 160000,
 (b) non-cross reactive with basic fibroblast growth factor, and
 (c) belonging to the immunoglobulin class IgG;
(2) a cloned hybridoma which,is derived from a splenic cell of a mammal immunized with aFGF protein and a homogenic or heterogenic lymphoid cell by cell fusion;
(3) a method for producing said cloned hybridoma which comprises fusing the homogenic or heterogenic lymphoid cell with the splenic cell from the mammal immunized with aFGF protein and selecting the desired hybridoma;
(4) a method for producing said monoclonal antibody which comprises culturing said cloned hybridoma in either a medium or an abdominal cavity of a mammal to produce the monoclonal antibody and collecting the monoclonal antibody ;
(5) a method for purifying aFGF protein which comprises contacting a sample containing aFGF protein with said monoclonal antibody; and
(6) a method for detecting or measuring aFGF protein which comprises using the monoclonal antibody defined in the above-mentioned item (1).

BRIEF DESCRIPTION OF THE DRAWINGS

FIG. 1 depicts a cDNA sequence for aFGF as used in Example 1.

FIG. 14 depicts an amino acid sequence of 5 amino terminal residue-deleted haFGF mutein obtained in Reference Example 3. In FIG. 14, M at the N terminus stands for methionine derived from the intiation codon.

FIG. 15 depicts an amino acid sequence of 43 amino terminal residue-deleted haFGF mutein obtained in Reference Example 3. In FIG. 15, M at the N terminus stands for methionine derived from the intiation codon.

DETAILED DESCRIPTION OF THE INVENTION

Figure 2:
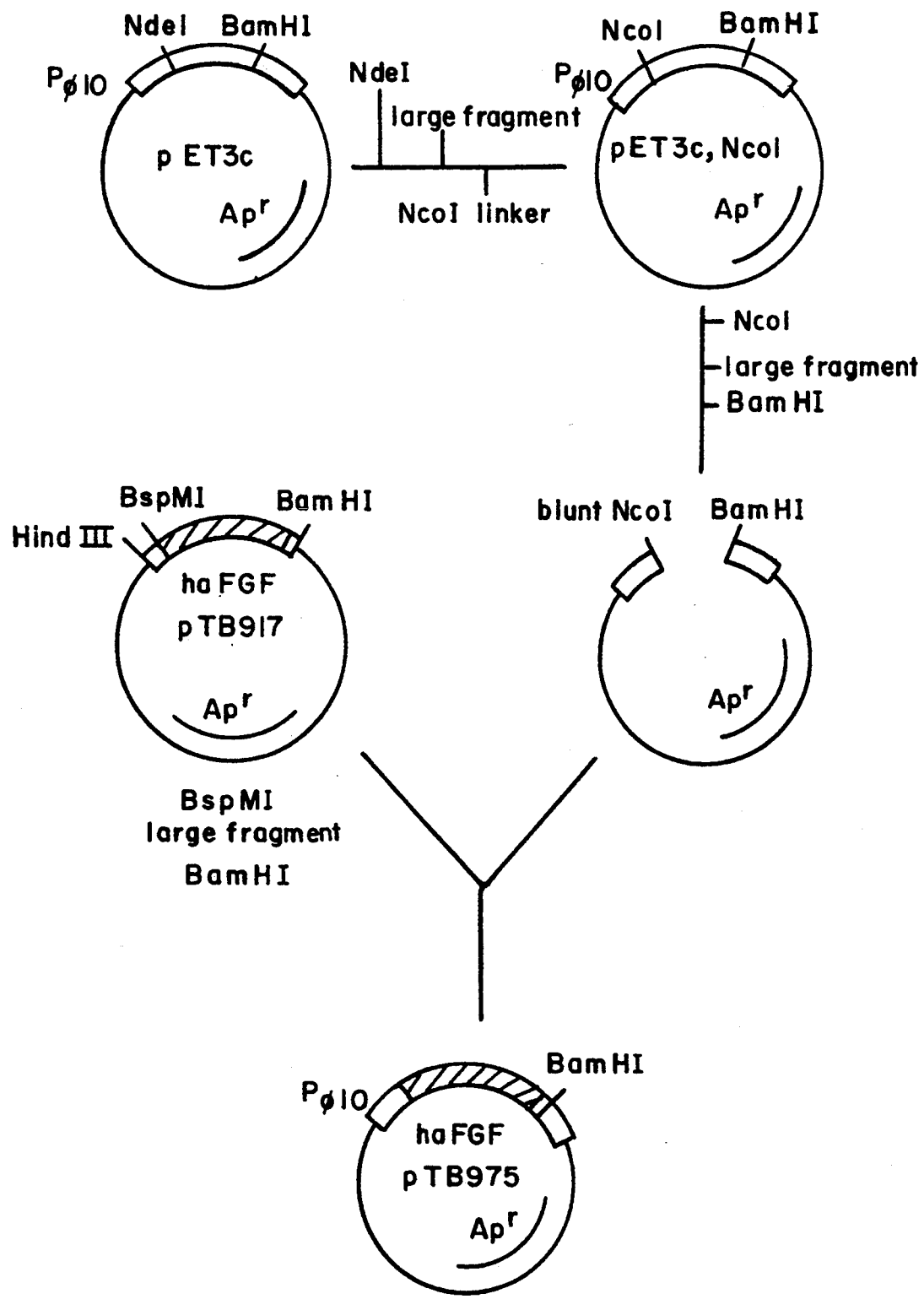
FIG. 2 shows a schematic illustration for construction of plasmid pTB975 as obtained in Example 1.

The aFGF proteins used for immunizing mammals in the present invention may include any aFGF derived from warm blooded mammals. The aFGF proteins which can be used in the present invention may include any muteins of aFGF.

The aFGF protein which can be used in the present invention includes a bovine aFGF (G. Gimenez-Gallego, et al., Science, 230: 1385 (1985) and F. Esch, et al., Biochemical and Biophysical Research Communications, Vol. 133: 544 (1985)), a human aFGF (G. Gimenez-Gallego, et al., Biochemical and Biophysical Research Communications, Vol. 138, 611 (1986)) and the like. The aFGF proteins used fop immunizing mammals in the present invention are preferably polypeptides which have amino acid sequences of human aFGF as disclosed in Biochemical and Biophysical Research Communications, Vol. 138, No. 2, pp. 611-617, (1986).

The aFGF proteins used for immunizing mammals in the present invention can be obtained by a method which comprises constructing an expression vector comprising a base sequence encoding the aFGF polypeptides, transforming a host with the vector, and culturing the resulting transformant in a medium to produce aFGF.

The expression vector used in the present invention can be produced, for example, by:

(a) isolating an RNA encoding aFGF;
(b) synthesizing a single-stranded complementary DNA (cDNA) from said RNA and then a double-stranded DNA;
(c) inserting said complementary DNA into a plasmid;
(d) transforming a host with,the resultant recombinant plasmid;
(e) cultivating the transformant thus obtained, then isolating the plasmid which contains the desired DNA from the transformant by an appropriate method, for example, the colony hybridization using a DNA probe;
(f) cleaving the desired cloned DNA from said plasmid; and
(g) ligating said cloned DNA fragment with a vehicle at a site downstream from a promoter.

The RNA encoding aFGF can be obtained from a wide variety of aFGF-producing tissues, for example, a human brain tissue and a human retinal tissue.

The human aFGF can be prepared by inserting the expression vector thus obtained into an appropriate host (e.g., *Escherichia coli, Bacillus subtilis*, yeasts, animal cells), and cultivating the resultant transformant in a medium.

The muteins of aFGF which can be used in the present invention are either peptides or proteins in which a part of amino acid sequence is changed, deleted, and/or added.

The muteins of aFGF which can be used in the present invention are those having aFGF activity.

Such mutation may include amino acid additions of amino acid(s), deletions of constituent amino acid(s) or substitutions of constituent amino acid(s) by other amino acid(s).

Amino acid addition means adding at least one amino acid thereto. Amino acid deletion means deleting at least one constituent amino acid therefrom.

In the present mutein which lacks at least one aFGF-constituent amino acid, the number of deleted amino acids may be any one as long as the mutein keeps the characteristics of aFGF.

The deleted-type muteins are preferably those comprising continuous polypeptides consisting of from 90 to 133 amino acids of aFGF, more preferably those comprising continuous polypeptides consisting of from 120 to 131 amino acids of aFGF, still more preferably those comprising continuous polypeptides consisting of from 125 to 131 amino acids of aFGF or those comprising continuous polypeptides consisting of from 131 to 133 amino acids of aFGF.

Such deleted-type muteins are preferably those lacking amino acids from the N-terminus of mature aFGF. Such deleted-type muteins can lack up to 3 amino acids from the C-terminus of mature aFGF. Examples of said deleted-type muteins may include, for example, those lacking any of 8 amino acids, 9 amino acids, 11 amino acids, 12 amino acids, 20 amino acids, and 43 amino acids from the N-terminus of human aFGF.

Furthermore, the deleted-type muteins may include those which lack 5 amino acids or 1 amino acid from the N-terminus of human aFGF, those which lack 6 amino acids from the N-terminus of bovine aFGF, muteins which comprise an amino acid sequence residing either between positions 1 and 15, between 114 and 140, or between 7 and 41 of bovine aFGF (numbered from the N-terminus), those which comprise an amino acid sequence residing either between positions 1 and 41, or between 7 and 41 of human aFGF (numbered from the N-terminus), and the like.

Such substitution means substituting another amino acid fop at least one of aFGF-constituent amino acids therein.

Where the mutein in the present invention has at least one amino acid added to aFGF, the at least one amino acid therein excludes methionine derived from initiation codons used for expression of peptides and signal peptides. The number of added amino acids is at least one and it may be any one as long as the mutein keeps the characteristics of aFGF. Preferably, the added amino acids may include some or all of the amino acid sequences in proteins which are accepted to be homologous with aFGF and exhibit activities similar to those of aFGF.

In the present mutein where an aFGF-constituent amino acid is substituted by other amino acid, the number of the aFGF-constituent amino acids before substitution therein replaced is not limited, as long as the mutein keeps the characteristics of aFGF. Examples of the constituent amino acids before substitution may include cysteine and other amino acids and particularly preferably, cysteine. Examples of the constituent amino acid which is other than cysteine, includes aspartic acid, arginine, glycine, valine, and the like.

When the constituent amino acid before substitution is cysteine, the newly introduced amino acid is preferably, for example, a neutral amino acid. Examples of the neutral amino acid may include, for example, glycine, valine, alanine, leucine, isoleucine, tyrosine, phenylalanine, histidine, tryptophan, serine, threonine, methionine, and the like. Particularly preferred are serine and threonine.

When the constituent amino acid before substitution is other than cysteine, the newly introduced amino acid is, for example, selected from those different in hydrophilic or hydrophobic properties, or electric charge from the original amino acid before substitution.

When the constituent amino acid before substitution is aspartic acid, examples of the newly introduced amino acid may include asparagine, threonine, valine, phenylalanine, and arginine, and most preferably asparagine and arginine.

When the constituent amino acid before substitution is arginine, the introduced amino acid may include glutamine, threonine, leucine, phenylalanine, and aspartic acid, and most preferably glutamine.

When the constituent amino acid before substitution is glycine, the introduced amino acid may include threonine, leucine, phenylalanine, serine, glutamic acid, arginine, and the like, and most preferably threonine.

When the constituent amino acid before substitution is serine, the introduced amino acid may include methionine, alanine, leucine, cysteine, glutamine, arginine, aspartic acid, and the like, and most preferably methionine.

When the constituent amino acid before substitution is valine, the introduced amino acid may include serine, leucine, proline, glycine, lysine, aspartic acid, and the like, and most preferably, serine The constituent amino acid before substitution may include preferably aspartic acid, arginine, glycine, serine and valine. The introduced amino acid may include preferably asparagine, glutamine, arginine, threonine, methionine, serine, and leucine. Most preferred are substituted muteins in which cysteine, a constituent amino acid, is replaced by serine. In said substitution there may be two or more substitutions simultaneously. Most preferred is the substitution of 2 or 3 constituent amino acids.

The mutein can result from one or more of combinations of the above-mentioned additions, deletions and substitutions.

The muteins of aFGF which can be used in the present invention may include a human aFGF comprising one or more substitutions of the cysteine residues at positions 16, 83 and 117 of mature human aFGF with other amino acid(s) and/or an additional methionine attached to the first amino acid at the N-terminus of mature human aFGF.

Furthermore, the muteins of aFGF which can be used in the present invention may include a bovine aFGF mutein comprising one or more substitutions of the cysteine residues at positions 16, 47 and 83 of mature bovine aFGF with other amino acid(s) and/or an additional methionine attached to the first amino acid at the N-terminus of mature bovine aFGF.

Further, the muteins of aFGF which can be used in the present invention may include said human and/or bovine aFGF mutein(s) comprising 139, 140 or 154 amino acid sequences.

The mutein comprising 39 amino acids is equivalent to the 140 amino acid form with the amino terminal phenylalanine residue removed.

The mutein comprising 154 amino acids is equivalent to a mutein which contains the following additional amino acids:

Ala-Glu-Gly-Glu-Ile-Thr-Thr-Phe-Thr-Ala-Leu-Thr-Glu-Lys with the C-terminus Lys attached to the N-terminus Phe at the first position of the 140 amino acid form (EP No. 0 319 052).

For the preparation of said muteins, site-directed mutagenesis is applicable and useful. This technique is well known in the literature, for example, Lather, R. F. and Lecoq, J. P., Genetic Engineering, Academic Press, (1983), 31–50. The mutagenesis directed on oligonucleotides is described in Smith, M. and Gillam, S., Genetic Engineering; Principle and Method, Plenum Press, (1981), Vol.3, 1–32. The structural genes encoding the muteins may be prepared by, fop example,
  (a) hybridizing a single-stranded DNA comprising a single strand of aFGF structural gene, with an oligonucleotide primer having mutation (the primer is complementary to a region comprising a codon for cysteine to be replaced or, as the case may be, an anti-sense triplet pairing with the codon fop cysteine, except that mismatches with codons for other amino acids, and, as the case may be, anti-sense triplets are permitted),
  (b) elongating the primer with DNA polymerase to form a mutational heteroduplex having the mutation, and
  (c) replicating this mutational heteroduplex.

A phage DNA carrying the mutated gene is then isolated and inserted into a plasmid. The plasmid thus obtained is used for transformation of an appropriate host, and the resulting transformant is cultured in a medium under conditions suitable for expression of the muteins.

The mutein of aFGF which lacks at least one aFGF-constituent amino acid and can be used as a antigen in the present invention is preferably selected from those comprising more than 109 amino acids among the amino acid sequence of aFGF.

Upon immunization of said aFGF protein, the aFGF protein may be prepared in a complex form with a carrier protein before use.

Such carrier proteins include, for example, bovine serum albumin, bovine thyroglobulin, hemocyanin, and the like.

When a carrier protein complex is used, the coupling ratio of carrier protein to aFGF protein is about 0.1 to about 30 times (carrier/aFGF protein, ratio by weight). Preferably the ratio of about 0.5 to about 5 times is used.

For coupling between hapten and carrier, various coupling agents can be used, and glutaraldehyde, carbodiimide, etc. are more preferably used.

In immunizing mammals by means of aFGF protein or complex with carrier, laboratory animals such as sheep, goats, rabbits, guinea pigs, rats and mice may be used, and rats and mice, especially mice, are preferred for obtaining monoclonal antibodies. Immunization, for example when mice are immunized, is possible via any route such as subcutaneous, intraperitoneal, intravenous, intramuscular or intracutaneous injection, and preferably conducted by mainly either subcutaneous, intraperitoneal, or intravenous injection (in particular, subcutaneous injection). Immunizing interval, immunizing dose, etc. are also highly variable allowing various protocols to be used; for example, the method in which immunization is conducted about 2 to 6 times at intervals of 2 weeks, and about 2 to 5 days later, preferably about 2 to 4 days after the final immunization are carried out, spleen cells taken out, is commonly used. It is desirable that an immunizing dose be more than about 0.µg, preferably about 10 µg to 300 µg for each mouse, calculated on the peptide amount basis, per each injection. It is also desirable that a fusion experiment using a spleen cell be carried out after verification of increase in blood antibody titer by local blood sampling prior to excision of the spleen.

In the above-mentioned cell fusion of a spleen cell with a lymphoid cell, an excised mouse spleen cell, for example, is fused with an appropriate homogenic or heterogenic (preferably homogenic) lymphoid cell line having a marker such as hypoxanthine-guanine phosphoribosyltransferase deficiency (HGPRT−) or thymidine kinase deficiency (TK−). As the lymphoid cell line, a myeloma cell is preferred, and the myeloma cell there is mentioned myeloma P3-X63-Ag.8UI (Ichimori et al.: Journal of Immunological Methods, 80, 55 (1985)). The fusion can be executed via e.g. the method developed by Köhler and Milstein (Nature, 256, 495 (1975)). For example, myeloma cells and spleen cells, in an about 1:5 ratio, are suspended in a medium prepared by mixing together Iscove's medium and Ham's F-12 medium in a 1:1 ratio (hereinafter referred to as IH medium), and a fusogen such as Sendai virus or polyethylene glycol (PEG) is used.

Of course, dimethyl sulfoxide (DMSO) and/or other fusion promoters can also be added. The following are normally used: a degree of polymerization for the PEG of about 1000 to 6000, a treating time of about 0.5 to 30 minutes and a PEG concentration of about 10 to 80% Efficient fusion can be achieved by about 4 to 10 minutes of PEG 6000 treatment at an about 35 to 55% concentration. The fused cells can be selectively propagated using the hypoxanthine-aminopterin-thymidine medium (HAT medium; Nature, 256, 495 (1975)).

The culture supernatant of the grown cells can be subjected to screening for the production of the desired antibody, and the screening for antibody titer can be conducted as follows:

The culture supernatant can first be assayed for the production of antibody against an immunized peptide by a method such as the radioimmunoassay (RIA) or enzyme immunoassay (EIA). Various modifications of these methods are also possible. As an example of the preferred assay, a method using EIA is described below.

To a carrier such as cellulose beads the rabbit anti-mouse immunoglobulin antibody, for example, is beforehand coupled in accordance with a routine method, and the culture supernatant to be assayed and mouse serum are added there to, and reaction is carried out at constant temperature (which means about 4° to 40° C; this definition also applied hereinafter) for the specified time.

After the reaction product is well washed, a peptide labeled with enzyme (prepared by coupling of an enzyme and a peptide in accordance with a routi method, followed by purification) is added, and reaction is carried out at constant temperature for the specified time. After the reaction product is well washed, an enzyme substrate is added, and reaction is carried out at constant temperature for the specified time, whereafter the resulting chromogenic substance can be assayed by absorptiometry or fluorometry.

It is desirable that the cells which show proliferation in the selective medium and secrete antibodies which combine with a peptide used for the immunization, are subjected to cloning by limiting dilution method, etc. The supernatant of the cloned cells is subjected to screening in the same manner as above to propagate cells in the well exhibiting high antibody titer, whereby monoclonal antibody producing hybridoma clones showing reactivity to the peptide used for the immunization are obtained.

The hybridoma thus cloned is grown in a culture medium, for example, RPMI-1640 Medium (Moore, G. E., et. al., Journal of American Medical Association, 199, 549 (1967)) supplemented with about 0.to 40% of bovine serum. Specifically, said monoclonal antibody can be obtained from the medium cultured for about 2 to 10 days, preferably about 3 to 5 days. The monoclonal antibody can also be obtained from ascitic fluids of mice which are intraperitoneally inoculated with the hybridoma. For this purpose, in the case of mice, for example, about $1 \times 10^4$ to $1 \times 10^7$, preferably about $5 \times 10^5$ to $2 \times 10^6$ hybridoma cells are intraperitoneally inoculated into a mouse such as BALB/c, which is previously inoculated with mineral oil etc., and about 7 to 20 days later, preferably about 10 to 14 days later, ascitic fluid is collected. The monoclonal antibody produced and accumulated in the ascites is subjected to, for example, ammonium sulfate fractionation and DEAE-cellulose column chromatography, whereby the desired monoclonal antibody can easily be isolated as a pure immunoglobulin.

According to the present invention, a monoclonal antibody which binds specifically with aFGF protein is thus obtained. The monoclonal antibody according to the present invention binds specifically with the immunogen peptide of aFGF protein. The monoclonal antibody according to the present invention may also bind with an aFGF protein other than the immunogen peptide.

Since binding specifically with aFGF protein, the monoclonal antibody according to the present invention is very useful as a reagent for an aFGF protein assay. It also facilitates aFGF protein assay in living organs and tissues, so it is very useful in obtaining fundamental information with regard to the aFGF protein (e.g., distribution in vivo).

For the detection of aFGF in living organs and tissues, either the quantitative measurement by an method and the like, a fluorescent antibody technique or a radioimmunoassay is generally employed. In order to measure an amount of aFGF protein in living organs and tissues, Western blotting for a protein is useful. In this method, a crude extract or partial purified sample of the extract is subjected to polyacrylamide gel electrophoresis, transferring to membrane filter, and then detection with HRP-coupled anti aFGF protein antibody.

In addition, it is thought that some cancer cells produce aFGF by themselves to continue their proliferation on the basis of the aFGF. When anti-aFGF antibody is allowed to act on such cancer, the proliferation-promoting aFGF is neutralized, and the antibody is expected to exhibit cancer cell proliferation inhibition, that is, to act as an anticancer substance.

Furthermore, the antibody can be used to determine the aFGF in an aFGF-producing cancer, so it can also be applied to cancer diagnostic reagents. Moreover, based on the avidity of the said antibody to aFGF, an antibody affinity column can be prepared to use the antibody as a reagent for aFGF purification.

The antibody molecule which is used for the detection and quantitative determination of aFGF may include IgG and its fractions (e.g. F(ab')₂, Fab', or Fab). The antibody molecule which is coupled directly with a label is preferably Fab'.

The monoclonal antibody according to the present invention can be employed as a reagent for immunochemical assay.

In the immunochemical assay, a simultaneously mixed use of two or more antibodies, more preferably three antibodies, results in better detection sensitivity.

An amount of aFGF protein in living organs and tissues can be measured by the immunochemical assay for aFGF protein and thereby, as previously mentioned, it is thought that such assay is very useful in diagnosis for cancer, for example, through the measurement of vascularization factors in various tissues and body fluids.

The anti-aFGF protein-antibody is preferably used as an antibody conjugated on carriers.

The label-conjugated antibody which is employed in the assay according to the present invention is selected from anti-aFGF-antibodies that are coupled directly with a label on and have a different antigenic determinant site from the above-mentioned antibody conjugated on carriers. The anti-aFGF protein-antibody which is employed in the immunochemical assay according to the present invention may be any one as long as it is capable of binding to aFGF protein. The carriers on which the antibody according to the present invention is conjugated for the assay of aFGF protein may include gel particles (e.g. Sepharose 4B, Sepharose 6B (Pharmacia Finechemical, Sweden)), dextran gels (e.g. Sephadex G-75, Sephadex G-100, Sephadex G-200, (Pharmacia Finechemical, Sweden)), polyacrylamide gels (e.g. Biogel P-30, Biogel P-60, Biogel P-100, (Bio Rad Laboratories, U.S.A.)), celluloseparticles (e.g. Avicel (Asahikasei, Japan), ion exchangecellulose (e.g. diethylaminocellulose, carboxydimethylcellulose)), physical adsorbents (e.g. glasses (e.g. glass balls, glass rods, aminoalkylglass balls, aminoalkylglass rods), silicon chips, styrenic resins (e.g. polystyrene balls, polystyrene particles), immunoassay plates (e.g. Nunc, Denmark), ion exchange resins (e.g. weak acidic cation ion exchange resin (e.g. Amberlite IRC-50 (Rome and Haas, U.S.A.), Zeocarb 226 (Permtit, West Germany)), weak basic anion ion exchange resin (e.g. Amberlite IR-4B, Dowex 3 (Dow Chemical, U.S.A.))), and the like.

Coupling of the antibody onto the carrier is conducted according to conventional methods such as, for example, the cyanogen bromide coupling method and the glutaraldehyde method as described in Taisha (Japan), Vol.8, (1971) 696. The simple, convenient coupling may be carried out by physically adsorbing tile antibody on the surface of carrier.

The labels with which the antibody is coupled may include radio-isotopes, enzymes, fluorescent reagents, luminescent reagents, and the like, and are preferably enzymes. The enzyme is preferably selected from those which are stable and specifically active. The enzymes may include peroxidases, alkaline phosphatases, $\beta$-D-galactosidases, glucoseoxidases, and the like, and are preferably peroxidases. The peroxidases can be selected from those derived from various sources such as, fop example, horseradish, pineapple, fig, sugarcane, fava bean, corn. Preferably the peroxidase used in the present invention is horseradish peroxidase (HRP) extracted from horseradish. Upon coupling of the antibody with the label, the use of peroxidase previously maleimidated is convenient For utilizing the thiol group of the antibody molecule, Fab 2. Maleimide groups can be introduced via the amino group of peroxidase. For this purpose, N-succinimidyl-maleimido-carboxylate derivatives can be employed, and preferably N-($\gamma$-maleimidobutyloxy) succinimide (hereinafter also referred to as GMBS) is used. Thus some groups are allowed to be between the maleimide and the peroxidase. GMBS is preferably reacted with peroxidase in a buffer of pH From about 6 to about 8 at temperature of From about 10 to about 50° C. for about 10 min. to about 24 hours. The buffer includes, for example, 0.1M phosphate buffer (pH 7.0) and the like.

The maleimidated peroxidase thus obtained can be purified, for example, by gel chromatography and the like. The carriers used in the gel chromatography may include, for example, Sephadex G-25 (Pharmacia Finechemical, Sweden), Biogel P-2 (Bio Red Laboratories, U.S.A.), and the like. Maleimidated peroxidase is preferably reacted with antibody in a buffer at temperature of from about 0 ° to about 40° C. for about 1 to about 48 hours.

The buffer includes, for example, 0.1M phosphate buffer (pH 6.0) containing 5 mM ethylenediaminetetraacetate sodium salt and the like.

The peroxidase-labeled antibody thus obtained can be purified, for example, by gel chromatography and the like. The carriers used in the gel chromatography may include, for example, Sephadex G-25 (Pharmacia Finechemical, Sweden), Biogel P-2 (Bio Red Laboratories, U.S.A.), and the like. Maleimidated antibody can also be reacted via introduction of a thiol group into peroxidase.

Direct coupling of enzymes other than peroxidase with the antibody can be conducted according to the same manner as that of peroxidase and also by the known techniques such as the glutaraldehyde method, the periodate method, the aqueous carbodiimide method, and the like.

The sample to be assayed in the determination system according to the present invention may include body fluids such as urine, serum, plasma, spinal fluid, Fluids extracted from animal cells and micro-organisms, and supernatants from cultures thereof. The assay according to the present invention is illustrated in the following by using peroxidase as the label, but not limited to.

(1) To an antibody bound on a carrier is added a subject sample to be assayed and antibody-antigen reaction is conducted, followed by addition of the peroxidase labeled anti-aFGF-antibody conjugates obtained above and further antibody-antigen reaction.

The sample to be assayed in the above-mentioned determination system includes body fluids such as urine, serum, plasma, spinal fluid, fluids extracted from animal cells and micro-organisms, and supernatants from cultures thereof.

(2) To the reaction products obtained above is added a substrate for peroxidase and the above-mentioned reaction products are assayed for enzyme activity by measuring the absorbance or fluorescence of the resulting substance.

(3) Standard aFGF protein solutions with a known amount are previously assayed by the above mentioned processes (1) and (2), and the relation between aFGF and the absorbance or fluorescence is calibrated.

(4) An amount of aFGF in the subject sample which is containing an unknown amount of aFGF (sample to be assayed) is determined by applying intensities in the resulting absorbance or fluorescence of the subject sample to calibration curves.

When the monoclonal antibody of the present invention is employed in a detecting or measuring systems, it brings about a high sensitivity. Therefore, the system can measure whether aFGF is produced in an extremely small quantity from a cancer cell.

Purification of aFGF protein can be achieved by using carrier complexes coupled with the monoclonal antibody against an aFGF protein. Such purification is carried out by affinity chromatography procedures using the monoclonal antibody. Briefly, preferred purification procedures involve, for example, coupling the monoclonal antibody on an appropriate carrier, packing the resultant carrier in a column, passing a sample solution containing aFGF protein through the column to adsorb aFGF protein, and eluting.

The carriers which can be used in these procedures may include those as mentioned above. Particularly preferable are gel particles and various synthetic resins. Examples of the carrier are CNBr-activated Sepharose 4B (Pharmacia Finechemical, Sweden), Affi-Gel-10, Affi-Gel-15 (Bio Rad Laboratories, U.S.A.), and the like.

Coupling of the antibody onto the carrier is conducted according to conventional methods such as, for example, the cyanogen bromide coupling method and the glutaraldehyde method as described in Taisha (Japan), Vol.8, (1971) 696. This coupling can also be conducted by the other known techniques such as the aqueous carbodiimide method, the active ester method, and the like. Further, the simple, convenient coupling may be carried out by physically adsorbing the antibody on the surface of carrier.

In purification procedures using the abovementioned antibody column, the sample solution containing aFGF protein in a neutral or near buffer is adsorbed on the antibody column packed with antibody coupled. Thereafter, the column is washed with the same buffer, and specifically adsorbed aFGF protein is then eluted. As eluents, there can be used, for example, low or high pH buffer solutions and buffer solutions containing a high concentration of salt. The low pH buffer solution may be exemplified by 0.17M glycine-hydrochloric acid buffer (pH 2.3), 0.1M disodium citrate-hydrochloric acid buffer (pH 1.8), and the like. The high pH buffer solution may be exemplified by aqueous ammonium solution (pH 11), 0.2M sodium borate buffer (pH 11.7), and the like. The high concentration salt buffer solution may be exemplified by 6M guanidine-hydrochloric acid solution, 7M urea solution, and the like. The elution can be achieved by either a batch method or a method using a column.

The resulting eluates can be subjected to, for example, dialysis for further purification. For example, when obtained by the low pH buffer solution, the eluate is dialyzed against, for example, 0.1M sodium carbonate buffer (pH 10.5), and when obtained by the high pH buffer solution, the eluate is dialyzed against, for example, 0.02M phosphate-sodium chloride buffer (pH 8.0) containing 0.1% NaN$_3$ after neutralization with, for example, 0.1M glycine-hydrochloric acid buffer (pH 3.0).

The eluate obtained by using the high concentration salt buffer can be directly dialyzed against the abovementioned phosphate-sodium chloride buffer and stored.

The resulting eluates and dialyzed solution can be lyophilized and stored as a dry powder.

The aFGF protein thus purified exhibits an extremely high unit of activity, so it can be used, for example as a cure promoting agent for burns, wounds, etc. Furthermore since it possesses growth promoting activity of nerve cells, it is useful in treating various neuropathies.

For its pharmaceutical use, the aFGF protein can be safely administered to warm-blooded mammals (e.g. humans, mice, rats, hamsters, rabbits, dogs, cats) parenterally or orally either in a powder form per se or in the form of pharmaceutical compositions (e,g, injections, tablets, capsules, solutions, ointments) in admixture with pharmaceutical acceptable carriers, excipients and/or diluents. The pharmaceutical compositions can be formulated in accordance with a conventional method.

When used for the above pharmaceutical purposes, the aFGF protein is administered, for example, to the above warm-blooded mammals in an appropriate amount selected from the range of from about 10 ng to 10 μg/kg body weight a day according to route of administration, reaction sensitivities, severity of the disease, etc.

Further, the aFGF protein thus purified can be used as a reagent for promoting cell cultivation. In this instance, the aFGF protein is added to the medium preferably in an amount of about 0.1 to 10 μg per liter of medium.

In the specification and drawings of the present application, the abbreviations used for bases, amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

DNA: Deoxyribonucleic acid
cDNA: Complementary deoxyribonucleic acid
A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediamine tetraacetic acid
SDS: Sodium dodecyl sulfate
G, Gly: Glycine
A, Ala: Alanine
V, Val: Valine
L, Leu: Leucine
r, Ile: Isoleucine
S, Ser: Serine
T, Thr: Threonine
C, Cys: Cysteine
M, Met: Metionine
E, Glu: Glutamic acid
D, Asp: Aspartic acid
K, Lys: Lysine
R, Arg: Arginine
H, His: Histidine
F, Phe: Pheylalanine
Y, Tyr: Tyrosine
W, Trp: Tryptophan P, Pro: Proline
N, Asn: Asparagine
Q, Gln: Glutamine
ClZ: 2-Chlorobenzyloxycarbonyl
BrZ: 2-Bromobenzyloxycarbonyl
Bzl: Benzyl
Boc: Butoxycarbonyl The numbering of constituent amino acids in human and bovine aFGF used therein is in accordance with that described in Biochemical and Biophysical Research Communications Vol. 138, 611–617 (1986).

The following hybridomas which were obtained in the Examples mentioned below were deposited at the Institute for Fermentation, Osaka, Japan (IFO), and at the Fermentation Research Institute, Agency of Industrial Science and Technology, Ministry of International Trade and Industry, Japan (FRI) under the Budapest Treaty.

Their accession numbers on the deposit dates are shown in Table 1 below (The deposit dates are indicated in parenthesis). The FERM BP numbers given by FRI denote the accession numbers of the deposit under the Budapest Treaty.

TABLE 1

| Hybridoma | IFO | FRI |
|---|---|---|
| AF1-52 | IFO 50204 (August 9, 1989) | FERM BP-2607 (September 20, 1989) |
| AF1-81 | IFO 50205 (August 9, 1989) | FERM BP-2681 (December 13, 1989) |
| AF1-114 | IFO 50206 (August 9, 1989) | FERM BP-2608 (September 20, 1989) |
| HaF 1H11 | IFO 50198 (July 19, 1989) | |
| HaF 1E6 | IFO 50200 (July 24, 1989) | |
| HaF 1C10 | IFO 50197 (July 19, 1989) | FERM BP-2605 (September 20, 1989) |
| HaF 2F9 | IFO 50201 (July 24, 1989) | |
| HaF 2E6 | IFO 50202 (July 25, 1989) | FERM BP-2606 (September 20, 1989) |
| HaF 2B7 | IFO 50199 (July 24, 1989) | |
| HaF 1A10 | IFO 50203 (July 25, 1989) | |
| HaF 1F9 | IFO 50196 (July 19, 1989) | |

The recombinant human basic FGF (also, hereinafter briefly referred to as rhbFGF) which was used in the Examples mentioned below was prepared by the method as disclosed in European Patent Application Laid Open (also, hereinafter briefly referred to as EP) No. 237,966.

The rhbFGF was prepared and purified by using the transformant *Escherichia coli* K12 MM294/pTB 669 (IFO 14532, FERM BP-1281) according to the procedures described in Examples 1, 3 and 6 or 8 of EP No. 237,966.

The above-mentioned transformant *Escherichia coli* K12 MM294/pTB 669 was deposited at the Institute for Fermentation, Osaka, Japan (IFO), and at the Fermentation Research Institute, Agency of Industrial Science and Technology, Ministry of International Trade and Industry, Japan (FRI) under the Budapest Treaty.

Its accession numbers on the deposit dates are shown in Table 2 below (The deposit dates are indicated in parenthesis). As to the accession number given by FRI, FERM P number is first assigned to the domestic deposit which has been converted to the international deposit under the Budapest Treaty and the transformant has been stored at FRI under FERM BP.

TABLE 2

| Transformant | IFO | FRI |
|---|---|---|
| *E. coli* K12 MM294/pTB 669 | IFO 14532 (August 11 1986) | FERM P-8918 (August 21, 1986) FERM BP-1281 |

The transformants *E. coli* MM 294 (DE3)/pLysS, pTB975, *E. coli* MM 294 (DE3)/pLysS, pTB1069 and *E. coli* MM 294 (DE3)/pLysS, pTB1070, which were obtained in the Reference Examples 1, 3 and 3 mentioned below respectively were deposited at IFO, and they also were deposited at FRI under the Budapest Treaty.

Their accession numbers on the deposit dates are shown in Table 3 below (The deposit dates are indicated in parenthesis).

TABLE 3

| Transformant | IFO | FRI |
|---|---|---|
| *E. coli* MM294(DE3)/pLysS, pTB 975 (Reference Example 1) | IFO 14936 (September 12, 1989) | FERM BP-2599 (September 20, 1989) |
| *E. coli* MM294(DE3)/pLysS, pTB 1069 (Reference Example 3) | IFO 14937 (September 12, 1989) | FERM BP-2600 (September 20, 1989) |
| *E. coli* MM294(DE3)/pLysS, pTB 1070 (Reference Example 3) | IFO 14938 (September 12, 1989) | FERM BP-2601 (September 20, 1989) |
| *E. coli* K12 MM294/pTB 917 (Reference Example 1) | IFO 15093 (September 17, 1990) | |

EXAMPLES

The invention is further illustrated by the following Reference Examples and Examples. These examples are not intended to limit the invention in any manner.

Reference Example 1

Preparation of aFGF

Human aFGF was prepared by the procedures mentioned below by referring to the methods as described in Biotechnology, 5, 960 (1981); Journal of Biological Chemistry, 263, 16471 (1988); and ICSU Short Reports Volume 8, Advances in Gene Technology: Protein Engineering and Production, Proceedings of the 1988 Miami Bio/Technology Winter Symposium, IRL Press, page 110.

(a) Construction of Plasmid for Expression

Plasmid pTB917 carrying chemically synthesized cDNA for human aFGF (FIG. 1) in pUC18 (Methods in Enzymology, 101, 20–78 (1983)) was isolated from the transformant, *E. coli* K12 MM294/pT917 (IFO 15093) according to a conventional method. This plasmid pT917 digested with BspMI and treated with DNA polymerase large fragment to create blunt ends followed by digestion with BamHI to produce a 0.45 kb DNA fragment.

Plasmid pET-3c carrying $\phi$ 10 promoter of T7 phage (Studier, F. W. et al., J. Mol. Biol., 189, 130 (1986); Gene, 56, 125–135 (1987)) was used for a vector DNA. The pET-3c was cleaved with NdeI and treated with DNA polymerase large fragment to create blunt ends followed by ligation of NcoI linkers, 5′-CCATGG-3′ with T4 DNA ligase. The resulting plasmid was cleaved with NcoI and blunt-ended with DNA polymerase large fragment followed by cleavage with BamHI to remove S10 sequences. The resulting fragment was ligated with T4 DNA ligase to the 0.45 kb blunt-ended BspMI-BamHI fragment to give pTB975 (FIG. 2).

(b) Expression of Human aFGF cDNA in *E. coli*

λ phage DE 3 having T7 phage RNA polymerase gene [Studier, F. W. et al., J. Mol. Biol. 189, 113–130 (1986)] was lysogenized in *E. coli* MM 294 strains followed by transfection of plasmid pLysS carrying T7 phage lysozyme gene [Studier, F. W. et al., J. Mol. Biol 189, 113–130 (1986)] to produce *E. coli* MM 294 (DE3)/pLysS. The *E. coli* was transformed with pTB975 to give *E. coli* MM 294 (DE3)/pLysS, pTB975 (IFO 14936, FERN BP-2599).

The transformant was incubated in a medium containing 35 μg/ml of ampicillin and 10 μg/ml of chloramphenicol at 37° C. When the turbidity reached to Klett 170, isopropyl β-D-thiogalactoside (IPTG) was added to finally 0.5 mM. Incubation was continued for additional three hours.

The transformant were harvested by centrifugation, washed with PBS cooled in ice, recollected, and stored at −20° C. until use.

(c) Purification of Human aFGF

The microorganisms collected from 1 liter of culture were suspended in 100 ml of ice-cooled 10 mM Tris-HCl (pH 7.4) containing 10 mM EDTA, 0.6M NaCl, 10% sucrose and 0.25 mM PMSF, and egg white lysozyme was added to 0.5 mg/ml. The suspension was allowed to stand in ice for an hour, incubated at 37° C. for five minutes, sonicated (20 sec., twice), whilst ice cooling, and centrifuged (SORVALL, 18K rpm, 30 min., 4 ° C.) to give a supernatant. The supernatant was mixed with 200 ml of ice-cooled 20 mM Tris-HCl (pH 7.4) containing 1 mM EDTA, and applied to a heparin Sepharose column (2.5×4 cm) equilibrated in 20 mM Tris-HCl (pH 7.4) containing 1 mM EDTA and 0.2M NaCl. The column was washed with 150 ml of 20 mM Tris-HCl (pH 7.4) containing 1 mM EDTA and 0.5M NaCl, and then protein eluted with 20 mM Tris-HCl (pH 7.4) containing 1 mM EDTA and 1.5M NaCl.

Figure 3:
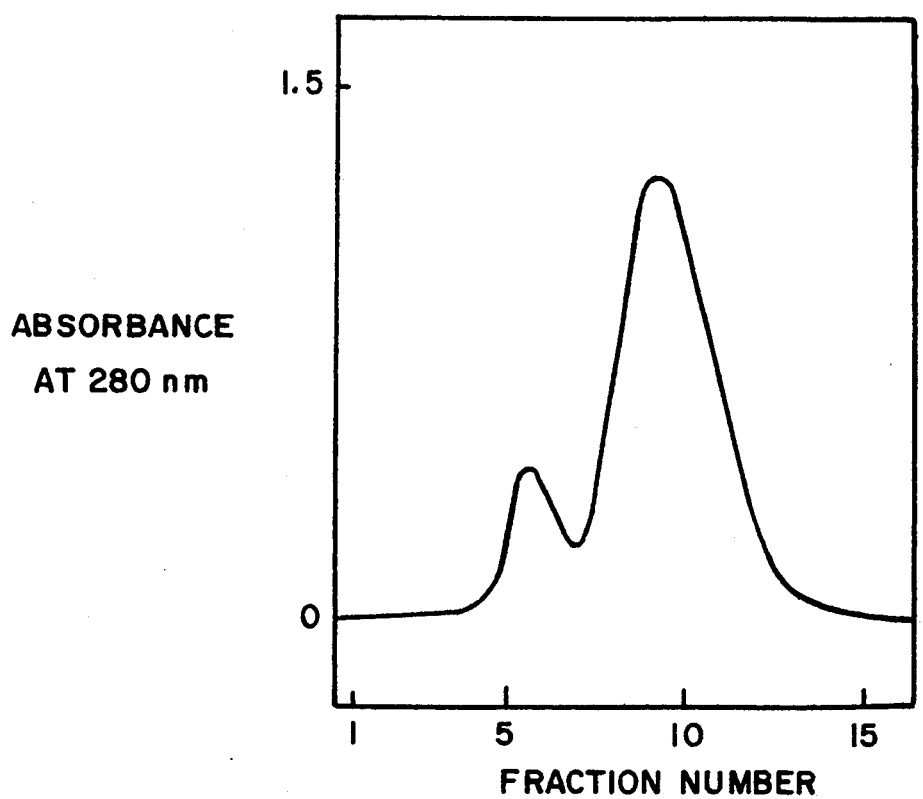
FIG. 3 depicts an elution profile obtained in Example 1.

Six ml fractions were collected, monitored at $OD_{280}$ and the second peak fractions (No.8-11, total 24 ml) were pooled (FIG. 3).

Twenty two ml of the eluate was mixed with an equivalent amount of 20 mM Tris-HCl (pH 7.4) containing 1 mM EDTA and 2M $(NH_4)_2SO_4$, and applied to a phenyl-Sepharose column (2.5×8 cm) equilibrated with 20 mM Tris-HCl (pH 7.4) containing 1 mM EDTA and 1M $(NH_4)_2SO_4$ (flow rate: 0.5 ml/min.).

The column was washed with 20 ml of the same buffer, and eluted with a linear gradient of from 1M to 0M ammonium sulfate (flow rate: 0.5 ml/min., for 200 min.).

Figure 4:
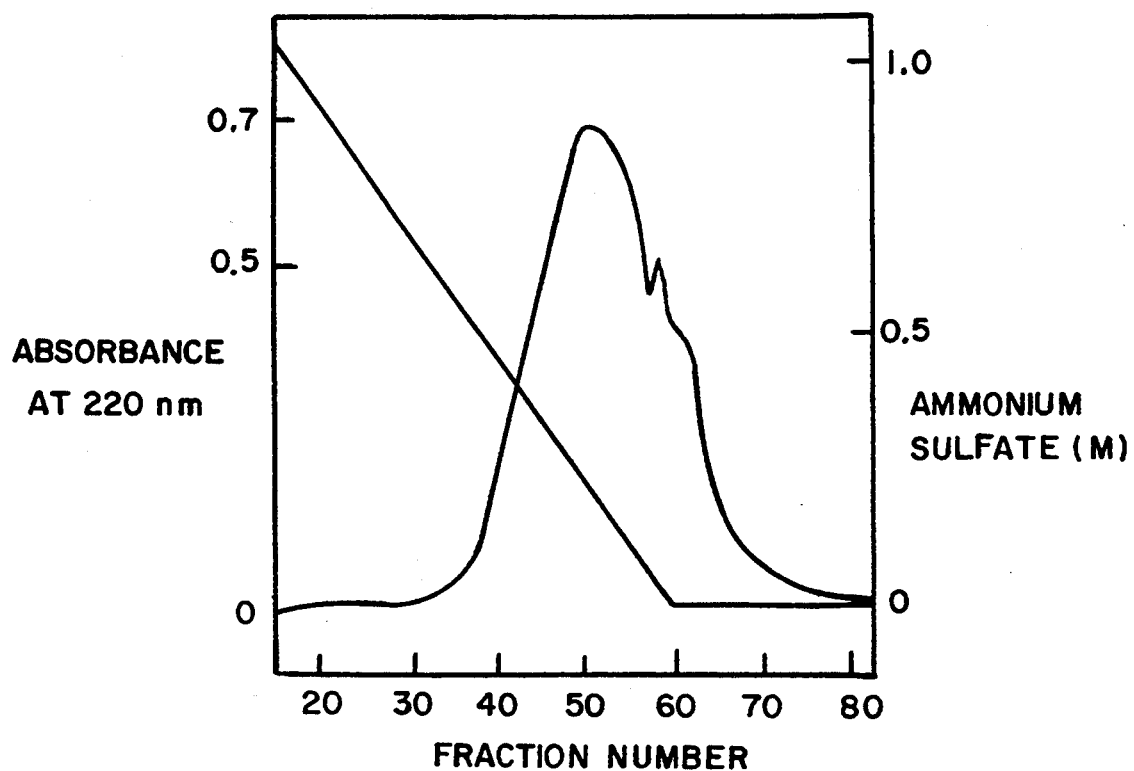
FIG. 4 depicts an elution profile obtained in Example 1.

Fractions 40–45 were collected (FIG. 4) as a purified aFGF.

(d) Reversed-Phase C4 HPLC

The solution (1.2 mg/ml) of purified human aFGF was mixed with 0.25 ml of 0.1% trifluoroacetic acid (TFA), applied on a reversed-phase C4 column (VYDAC), and eluted with a linear gradient of 0%–90% acetonitrile in 0.1% TFA.

Figure 5:
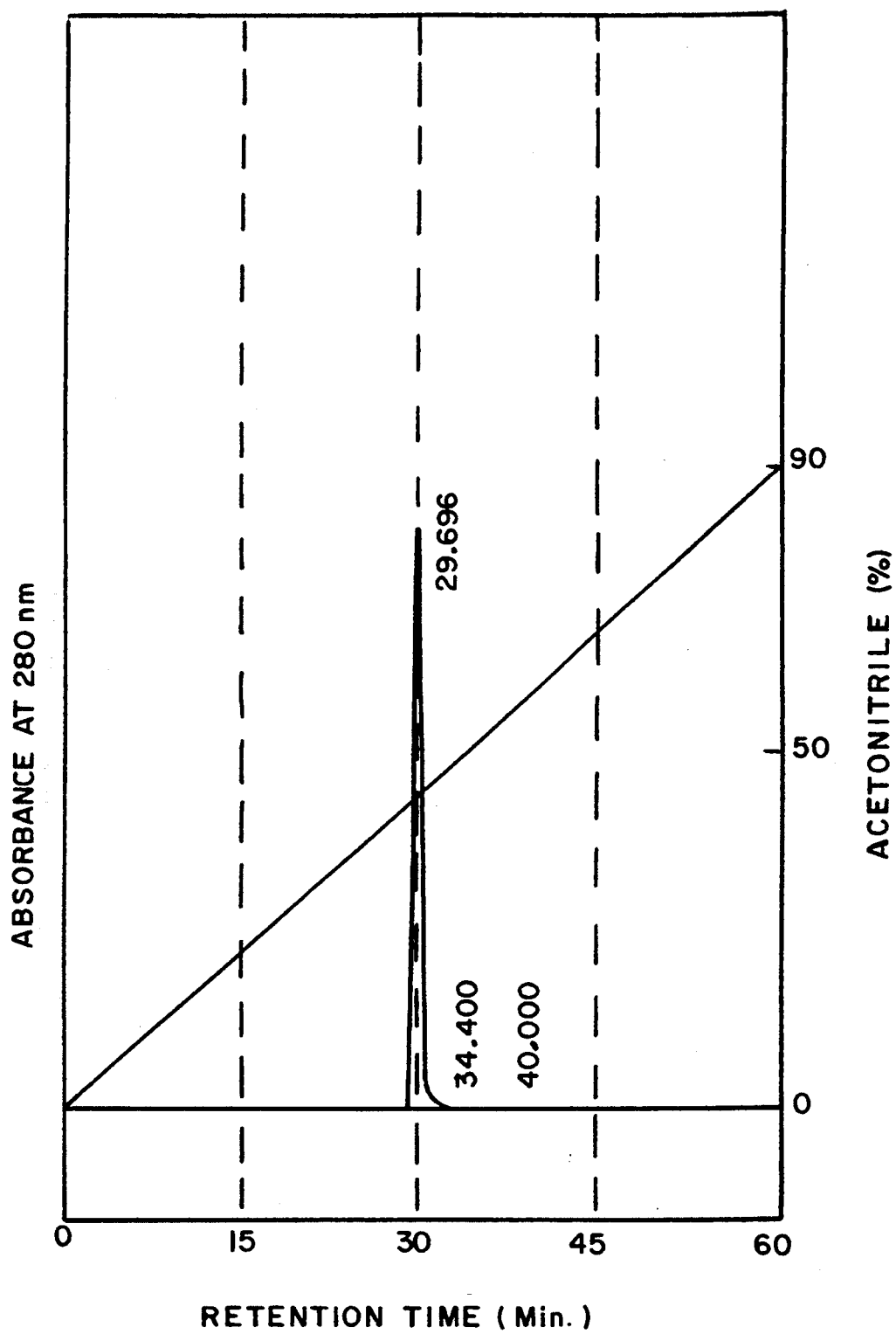
FIG. 5 depicts an elution profile obtained in Example 1.

The elution pattern was examined. The elution was performed at 1 ml/min. of flow rate for 60 min. (FIG. 5).

(e) Biological Activity

Activity of human aFGF was assayed by the determination of $^3$H-thymidine incorporation into DNA of mouse BALB/c 3T3 cell lines, in accordance with the method of Sasada, et al. (Mol. Cell Biol. 8, 588–594 (1988)). Upon addition of the sample, depending on necessity, a heparin solution (SIGMA Grade I) was added to media and the sample.

Reference Example 2

Preparation of Partial Human aFGF Peptide (1) Preparation of H-Phe-Asn-Leu-Pro-Pro-Gly-Asn-Tyr-Lys-OH (Human aFGF (1–9))

Boc-Lys(ClZ)-phenylacetamide(PAM)-resin (0.5 mmoles) was applied to Type 430A automatic peptide synthesizer (Applied Biosystems, U.S.A.) and the following amino acids were successively applied to condensation and de-t-butoxycarbonylation by using the synthesizer in the order listed below.

Boc-Tyr(BrZ)-OH
Boc-Asn-OH
Boc-Gly-OH
Boc-Pro-OH
Boc-Pro-OH
Boc-Leu-OH
Boc-Asn-OH
Boc-Phe-OH

Thus, 1.13 g of Boc-Phe-Asn-Leu-Pro-Pro-Gly-Asn-Tyr(BrZ)-Lys(ClZ)-PAM-resin was obtained. The peptide-resin was incubated in 13 ml of hydrogen fluoride containing 1.34 ml of anisole and 1.34 ml of dimethylsulfide at 0° C. for 60 minutes to give the peptide. The excess amount of hydrogen fluoride was removed by distillation under reduced pressure to give a residue. The residue was washed with diethyl ether and extracted with 50 ml of 1N acetic acid. The extract was subjected to ion-exchange using a column of Amberlite IRA-400 (acetate form)(2×5 cm). The eluate was lyophilized. The lyophilizate was dissolved in 10 ml of 30% acetic acid and purified by gel filtration employing Sephadex G-50 (Pharmacia, column: 5×110 cm, eluent: 30% acetic acid) to give a semi-pure product (267 mg).

The product was dissolved in 20 ml of 0.1N acetic acid and purified by ion-exchange chromatography employing CM-52 (Whatman, column: 2.2×18 cm, elution: linear gradient of 0.01M aqueous ammonium acetate solution (pH 4.5)-0.15M aqueous ammonium acetate solution (pH 6.5)) to give a product.

Yield: 213 mg Rf value: 0.50 ( n-butanol:pyridine:acetic acid: water=5:5:1:4) Amino acid analysis: Asp 1.98; Gly 1.00; Leu 0.99; Tyr 0.97; Phe 1.00; Lys 0.98; Pro 2.10

(2) Preparation of H-Leu-Pro-Leu-Pro-Val-Ser-Ser-Asp-OH (Human (bovine) aFGF (133–140))

Boc-Asp(OBzl)-PAM-resin (0.5 mmoles) was applied to Type 430A automatic peptide synthesizer (Applied Biosystems, U.S.A.) and the following amino acids were successively applied to condensation and de-t-butoxycarbonylation by using the synthesizer in the order listed below.

Boc-Ser(Bzl)-OH
Boc-Ser(Bzl)-OH
Boc-Val-OH
Boc-Pro-OH
Boc-Leu-OH
Boc-Pro-OH

Boc-Leu-OH

Thus, 1.10 g of Boc-Leu-Pro-Leu-Pro-Val-Ser(Bzl)-Ser(Bzl)-Asp(OBzl)-PAM-resin was obtained. The peptide-resin (500 mg) was incubated in 6.0 ml of hydrogen fluoride containing 0.6 ml of anisole and 0.6 ml of dimethylsulfide at 0° C. for 60 minutes to give the peptide. The excess amount of hydrogen fluoride was removed by distillation under reduced pressure to give a residue. The residue was washed with diethyl ether and extracted with 40 ml of 1N acetic acid. The extract was subjected to ion-exchange using a column of Amberlite IRA-400 (acetate form)(2×5 cm). The eluate was lyophilized. The lyophilizate was dissolved in 5 ml of 1N acetic acid and purified by gel filtration employing Sephadex LH-20 (Pharmacia, column: 2.5×125 cm, eluent: 1N acetic acid) to give a product.

Yield: 120 mg Rf value: 0.43 (ethyl acetate:butanol:acetic acid: water=1:1:1:1) Amino acid analysis: Asp 1.00; Ser 1.95; Pro 2.06 Val 0.98; Leu 2.01

Reference Example 3

Figure 6:
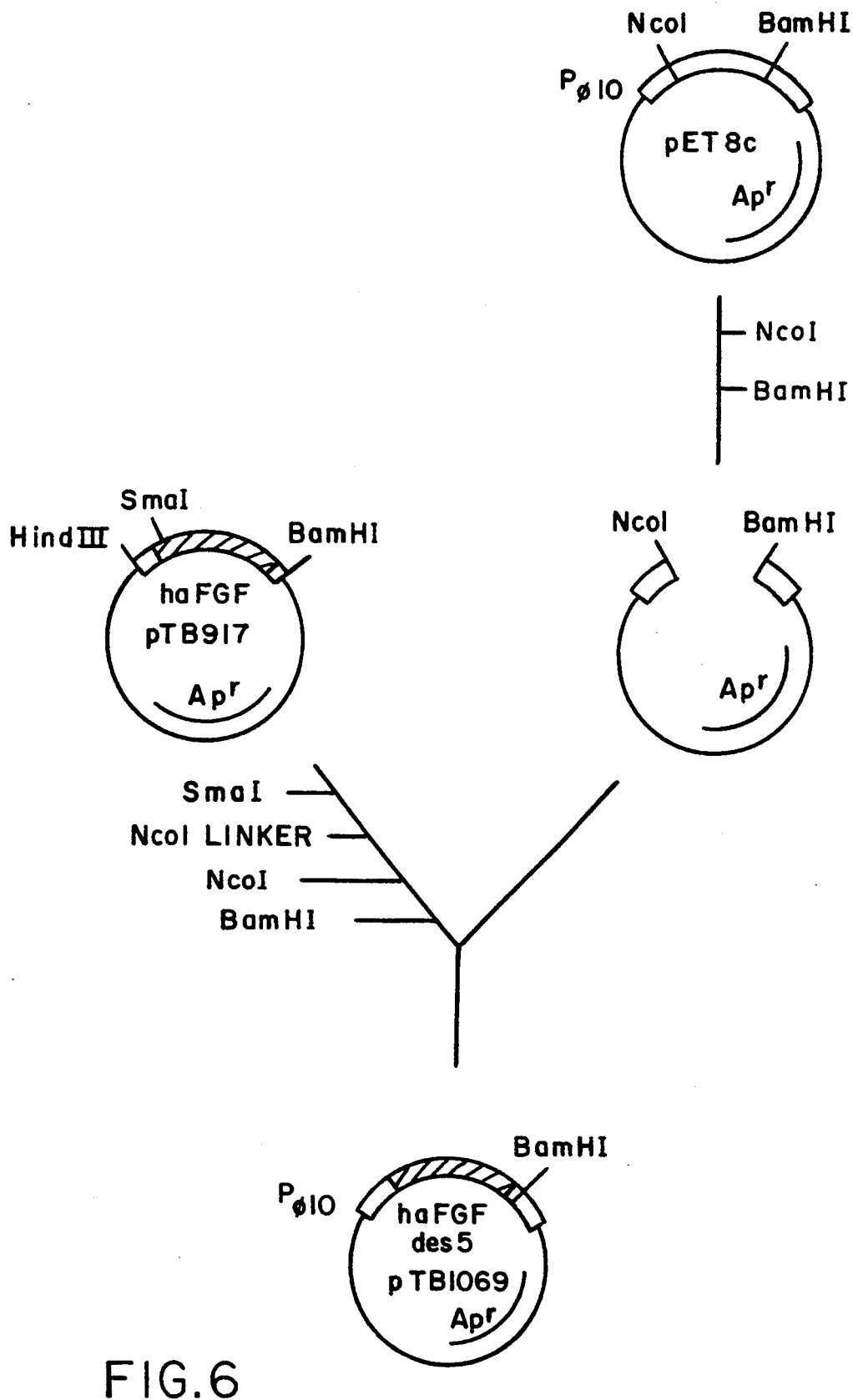
FIG. 6 shows a schematic illustration for construction of plasmid pTB1069 for the expression of 5 amino terminal residue-deleted aFGF as obtained in Example 3.
Figure 7:
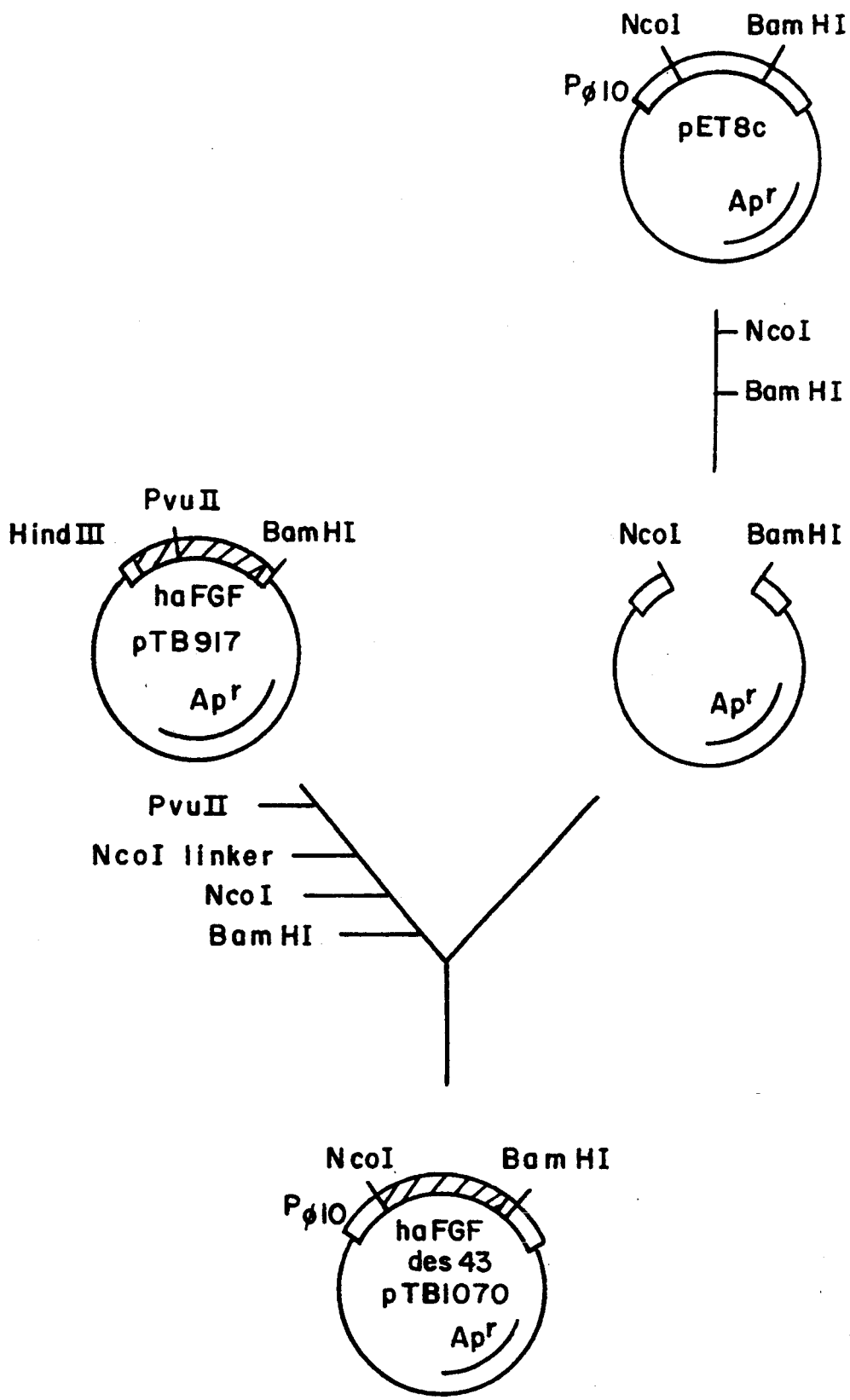
FIG. 7 shows a schematic illustration for construction of plasmid pTB1070 for the expression of 43 amino terminal residue-deleted aFGF as obtained in Example 3.

Preparation of Recombinant Human aFGF Mutein Deleted Amino Termini (a) Construction of Plasmid for Expression Plasmid pTB917 carrying chemically synthesized cDNA of human aFGF (FIG. 1) in pUC81 [Methods in Enzymology, 101, 20–78 (1983)] was cleaved with either SmaI (FIG. 6) or PuvII (FIG. 7), followed by ligation of NcoI linkers, 5'-CCATGG-3' with T4 DNA ligase. These plasmids were cleaved with NcoI and BamHI to prepare 0.41 kb and 0.3 kb DNA fragments.

Plasmid pET-8c carrying T7 phage φ 10 promoter (given by Studier, F. W. (Brookhaven National Labs U.S.A.), this pET-8c is described in J. Mol. Biol.189, 113–30 (1986); Gene, 56, 125–135 (1987)) was used for a vector DNA. The pET-8c was cleaved with NcoI and BamHI, followed by ligation of the 0.41 kb DNA fragment and the 0.3 kb thereto with T4 DNA ligase to obtain pTB1069 (FIG. 6) and pTB1070 (FIG. 7), respectively.

(b) Expression of haFGF cDNA Deleted Amino Termini in *E. coli*

λ phage DE3 having T7 phage RNA polymerase gene [Studier, F. W. et al., J. Mol. Biol. 189, 113–130 (1986)] was lysogenized in *E. coli* MM 294 strains followed by transfection of plasmid pLysS carrying T7 phage lysozyme gene [Studier, F. W. et al., J. Mol. Biol. 189, 113–130 (1986)] to produce *E. coli* MM 294 (DE3)/pLysS.

The *E. coli* was transformed with pTB1069 and pTB1070 to give *E. coli* MM 294 (DE3)/pLysS, pTB1069 (IFO 14937, FERM BP-2600) and *E. coli* MM 294 (DE3)/pLysS, pTB1070 (IFO 14938, FERM BP-2601), respectively.

The transformant was incubated in a medium containing 35 μg/ml of ampicillin and 10 μg/ml of chloramphenicol at 37° C. When the turbidity reached to Klett 120, isopropyl β-D-thiogalactoside (IPTG) was added to finally 0.5 mM. Incubation was continued for additional two hours.

The transformants were harvested by centrifugation, washed with phosphate buffered saline (PBS) cooled in ice, then recollected, and stored at −20° C. until use.

(c) Purification of Five Amino Terminal Residue Deleted haFGF

*E. coli* MM 294 (DE3)/pLysS, pTB1069 (IFO 4937, FERM BP-2600) collected from 75 ml of the culture was suspended in 10 ml of ice-cooled 10 mM Tris-HCl (pH 7.4) containing 10 mM EDTA, 0.2M NaCl, 10% sucrose and 0.25 mM phenylmethylsulfonyl fluoride (PMSF), followed by addition of egg white lysozyme to 0.5 mg/ml.

The suspension was allowed to stand in ice for an hour, then incubated at 37° C. for five minutes, sonicated whilst ice cooling, and centrifuged (SORVALL, 18K rpm, 30 min., 4° C. to give a supernatant. The supernatant was applied to a heparin HPLC column (0.8×5 cm) equilibrated in 20 mM Tris-HCl (pH 7.4). The column was washed with 20 mM Tris-HCl (pH 7.4) containing 0.6M NaCl, eluted with a linear gradient of from 0M to 2M NaCl (flow rate: 1 ml/min., for 1 hr.).

Figure 8:
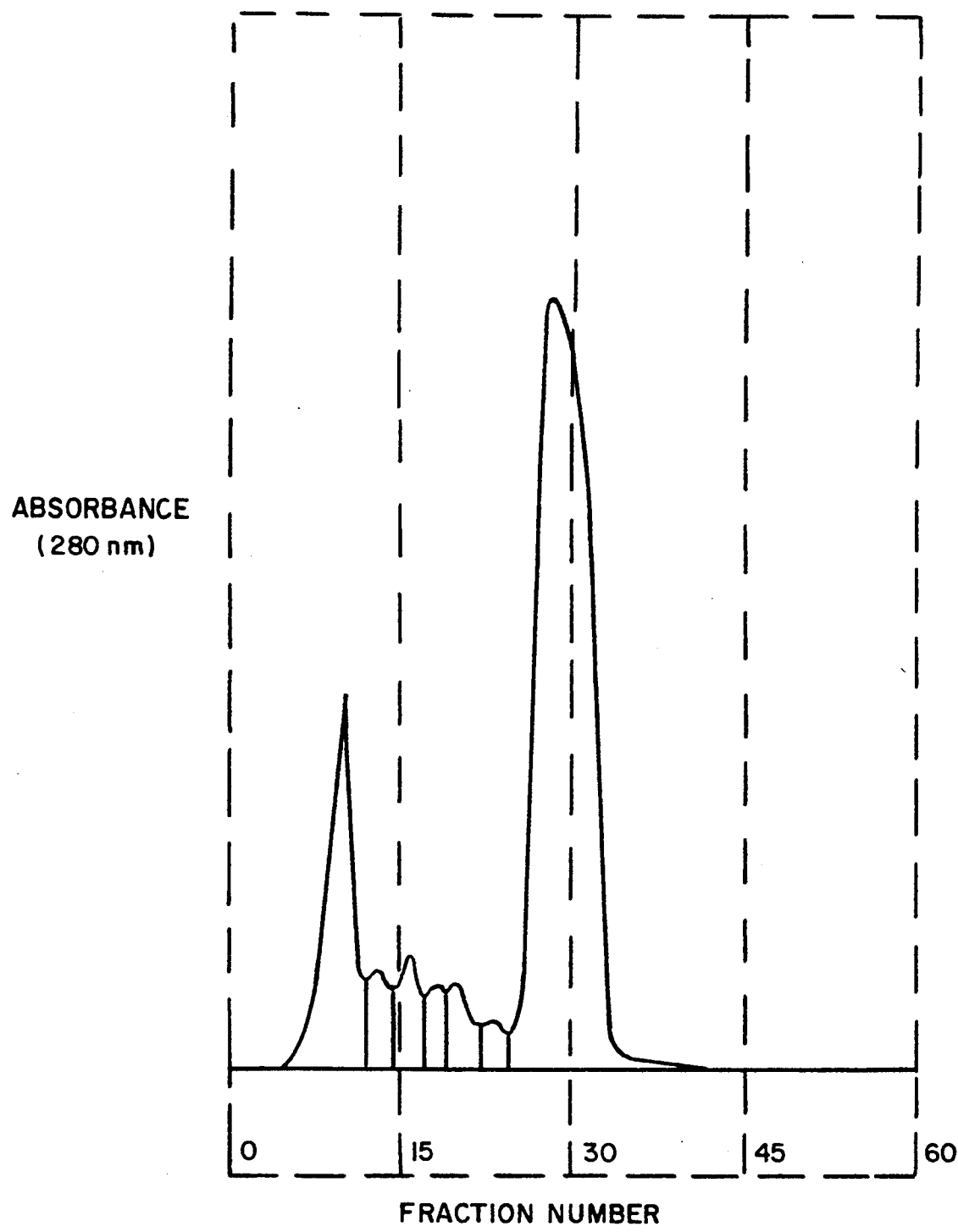
FIG. 8 depicts an elution profile from a heparin HPLC column used for purification of 5 amino terminal residue-deleted aFGF obtained in Example 3.

One ml fractions were collected. The eluted fractions 28–32 were pooled (FIG. 8).

Figures 14, 15:
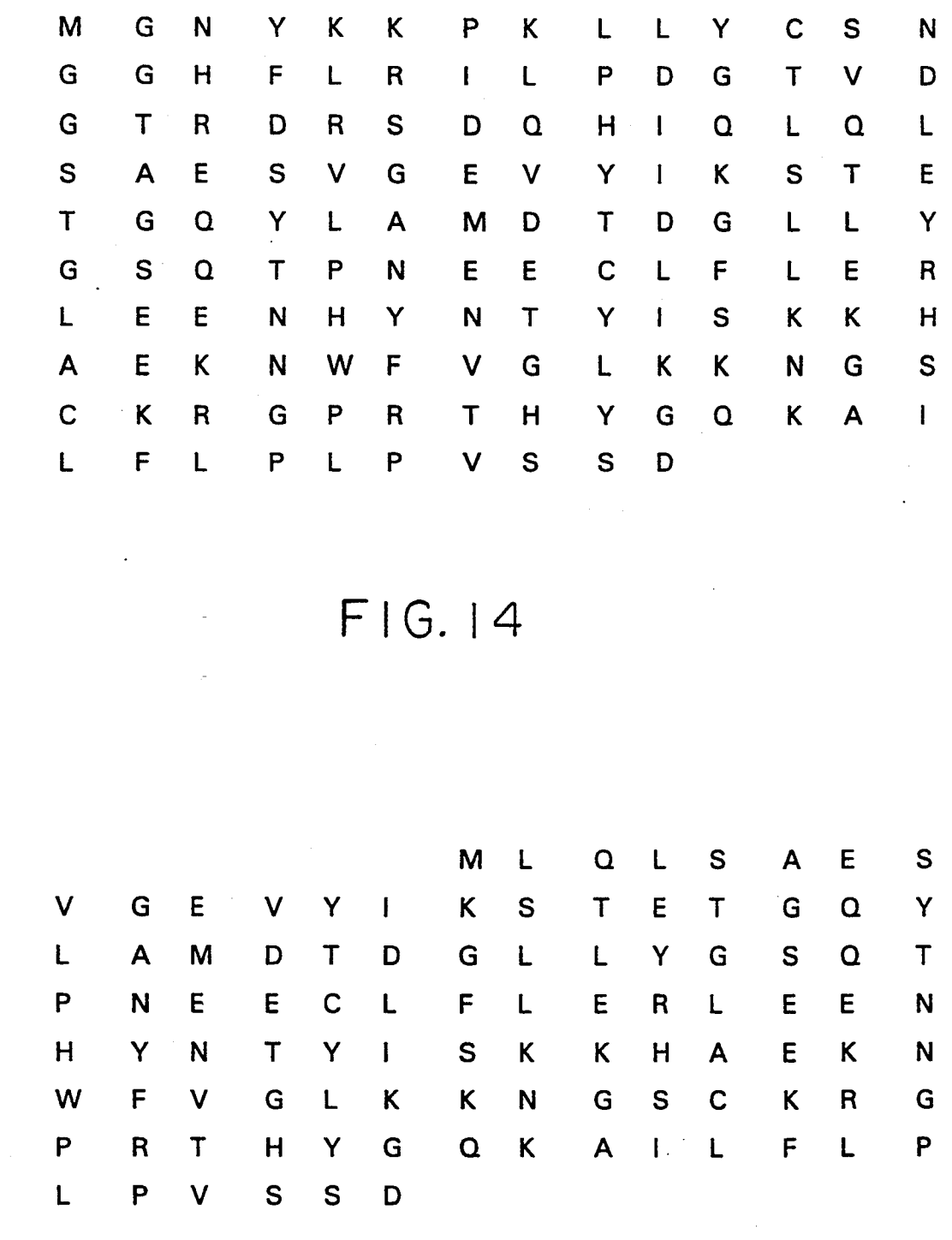

Five amino acid terminal residue deleted human aFGF (also, hereinafter briefly referred to as N5 deleted aFGF)(4.2 mg) which has the amino acid sequence as depicted in FIG. 14. was obtained by the above procedures.

(d) Purification of 43 Amino Terminal Residue Deleted haFGF

*E. coli* MM 294 (DE3)/pLysS, pTB1070 (IFO 14938, FERM BP-2601) collected from 125 ml of the culture was suspended in 10 ml of ice-cooled 10 mM Tris-HCl (pH 7.4) containing 10 mM EDTA, 0.2M NaCl, 10% sucrose and 0.25 mM phenylmethylsulfonyl fluoride (PMSF), followed by addition of egg white lysozyme to 0.5 mg/ml.

The suspension was allowed to stand in ice for an hour, then warmed to 37° C. for five minutes, sonicated whilst ice cooling, and centrifuged.

The precipitate was suspended in 2M NaCl followed by recentrifugation to give a precipitate which was suspended in 15 ml of 20 mM Tris-HCl (pH 7.4) containing 6M urea and 10 mM DTT, and incubated in ice for 3 hr. whilst intermittently stirring. The resulting solution was centrifuged to give a supernatant was applied to a Q-Sepharose column (2.5 cm×8 cm) equilibrated with 20 mM Tris-HCl (pH 7.4) containing 3M urea.

Figure 9:
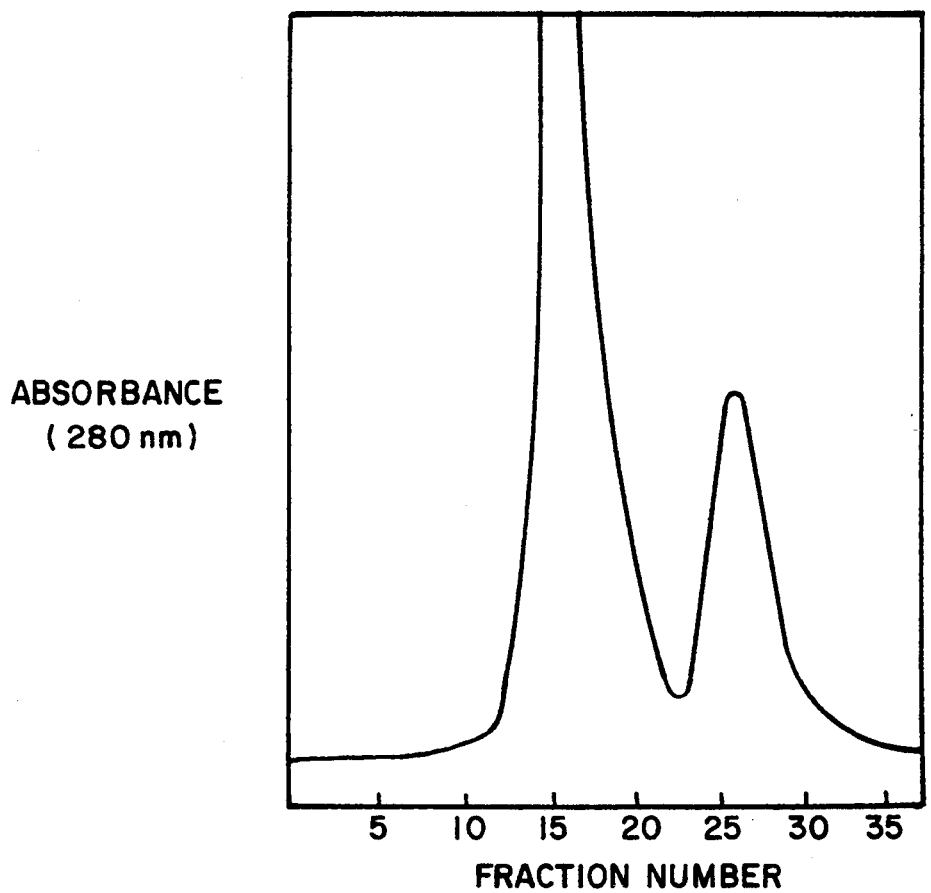
FIG. 9 depicts an elution profile from a Q Sepharose column used for purification of 43 amino terminal residue-deleted aFGF obtained in Example 3.

The column was washed with a buffer used for equilibrating, eluted with a linear gradient of from 0M to 1M NaCl at a flow rate of 0.6 ml/min. for 60 min. and 2.5 ml fractions were collected (FIG. 9). The eluted fractions 14–19 were pooled and dialyzed against 2 l of 20 mM Tris-HCl (pH 7.4) containing 5 mM DTT overnight followed by 3 l of 20 mM Tris-HCl (pH 7.4) containing 1 mM DTT for 3 hr. Fourty three amino terminal residue deleted human aFGF (also, hereinafter briefly referred to as N43 deleted aFGF)(3.2 mg) which has the amino acid sequence as depicted in FIG. 15. was obtained by the above procedures.

Example 1

(1) Immunization

BALB/c mice (female, 8-week old) were injected subcutaneously with 100 μg of human aFGF antigen (prepared in Reference Example 1) in 0.3 ml of physiological saline in admixture with an equivalent of Freund's complete adjuvant (Difco Laboratries, U.S.A.). Three weeks later, a mixture of an equivalent of the antigen and 0.3 ml of Freund's incomplete adjuvant was administered subcutaneously.

Further 3 weeks later, the similar additional immunization was carried out. Two weeks later, the mice were inoculated intravenously with 100 μg of human aFGF dissolved in a physiological saline.

(2) Cell fusion

The spleen was removed from the immunized mice three days after the final antigen challenge to obtain spleen cells to be used for cell fusion. These cells were suspended in a medium containing Iscove's medium and Ham's F-12 medium in a 1:1 ratio (hereinafter referred to as IH medium).

P3-X63-Ag. 8UI mouse myeloma cells were cultured in RPMI 1640 Medium containing 10% fetal calf serum under an atmosphere of 5% carbon dioxide and 95% air.

Cell fusion was conducted in accordance with the method as established by Köhler and Milstein (Nature, 256, 495 (1975)). The above myeloma cells ($3.2 \times 10^7$) were mixed with $1.6 \times 10^8$ immunized lymphocytes obtained by the above mentioned method and centrifuged, to which 45% polyethylene glycol 6000 (hereinafter referred to as PEG 6000) in 0.3 ml of IH medium was added dropwise.

The PEG 6000 solution was preheated to 37° C., and gradually added. Eight minutes later, 0.5 ml per minute of IH medium preheated to 37° C. was added to a final volume of 10 ml, and centrifuged at 600 rpm at room temperature for 15 minutes to remove a supernatant. The cell pellets were suspended in 100 ml of IH medium containing 20% fetal calf serum, and plated into 960 wells of 96-well microculture plates (Nunc) in an amount of 100 μl per well. One day later, IH medium (containing 20% fetal calf serum) supplemented with HAT ($1 \times 10^{-4}$M hypoxanthine, $4 \times 10^{-7}$M aminopterin, and $1.6 \times 10^{-5}$M thymidine)(hereinafter referred to as HAT medium) was added to the microculture plate in an amount of 100 μl per Nell, and further at intervals of three days one half amount of the medium was replaced with HAT medium. The cells thus grown are hybrid cells.

(3) Screening for Antibody-Producing Cell

The recombinant aFGF purified by the procedures as described in Reference Example 1 was diluted with 0.01M carbonate buffer (pH 8.5) to 10 μg/ml. The diluted solution was distributed into each well of 96-well microtiter plates (Nunc) in an amount of 100 μl and allowed to stand at 4° C. overnight in order to couple aFGF on the solid phase. The wells were washed with 0.01M phosphate buffer (pH 7.O) containing 0.0M NaCl. Thereafter, 200 μg/ml of 0.01M phosphate buffer containing 1% bovine serum albumin (BSA) was distributed into each well in order to block an excess of binding site, and stored at a chilled place until use.

To the 96-well microtiter plates coupled with aFGF as above-mentioned was added the hybridoma conditioned medium in an amount of 100 μl per well, incubated at room temperature for 2 hours. The conditioned medium was removed, and after washing, horseradish peroxidase (HRP)-labeled anti-mouse IgG goat antibody (Cappel) was added thereto as a secondary antibody, followed by incubation at room temperature for 2 hours.

The secondary antibody was removed, and after extensive washing of the wells, 100 μl of peroxidase substrate solution (sodium citrate buffer (pH 5.5) containing 0.02% $H_2O_2$ and 0.15% o-phenylenediamine) was added thereto, followed by incubation at 25° C. for 10 minutes.

After the enzyme reaction was quenched by adding 100 μl of 2N sulfuric acid, O. D. at 492 nm was measured by using an automatic microplate spectrometer (MTP-32, Corona)(ELISA).

The results of the above screening assay showed that 12 of the wells were positive for the presence of binding antibody.

(4) Cloning of Hybridoma

Cells in each of the wells were plated at a ratio of 0.5 cells per well onto wells of a 96-well microculture plates into which $5 \times 10^5$ cells per well of mouse thymocytes had been seeded as a feeder cell, and cloned.

As a result, one representative clone was obtained from each of these wells. A total of 12 clones were obtained and designated as follows:
AF1-52 (IFO 50204, FERM BP-2607),
AF1-81 (IFO 50205, FERM BP-2681),
AF113,
AF1-114 (IFO 50206, FERM BP-2608),
HaF 1H11 (IFO 50198),
1E6 (IFO 50200),
1C10 (IFO 50197, FERM BP-2605),
HaF 2F9 (IFO 5020),
HaF 2E6 (IFO 50202, FERN BP-2606),
HaF 2B7 (IFO 50199),
HaF 1A10 (IFO 50203),
HaF 1F9 (IFO 50196).

(5) Production of Antibody

The hybridoma clones obtained by the cloning of the above (4), AF1-52, AF1-81, AF1-113, AF1-114, HaF 1H11, HaF 1E6, HaF 1C10, HaF 2F9, HaF 2E6, HaF 2B7, HaF 1A10, and HaF 1F9 were inoculated at a number of $1 \times 10^6$ into the peritoneal cavities of BALB/c mice, previously injected intraperitoneally with 0.5 ml of mineral oil, respectively. Ten days after the peritoneal administration of hybridoma, ascitic fluids were collected.

Monoclonal antibodies were purified from about 10 ml of the resulting ascitic fluid according to the method of Staehelin, et al.(Journal of Biological Chemistry, 256, 9750–9754 (1981)).

The ascites were subjected to centrifugation at 10,000 rpm for 15 minutes to remove fibrin-like substances, and diluted with a phosphate-buffered saline (PBS: 8.1 mM $Na_2HPO_4$, 1.5 mM $KH_2PO_4$, 27 mM KCl, 137 mM NaCl, pH 7.2) to a concentration wherein UV absorbance at 280 nm ($A_{280}$) was from 12 to 14. After dilution, a saturated ammonium sulfate solution was, added to a concentration of 47%, subjected to salting-out at 4° C. for 60 minutes with stirring, and centrifuged (10,000 rpm, 15 minutes) to give a pellet. The pellet was dissolved in 20 mM Tris buffer (pH 7.9) containing 50 mM NaCl, and dialyzed against the same buffer. Two hours later, 2 l of fresh buffer was replaced and dialysis was continued for additional 15 hours.

Thereafter, the solution was centrifuged at 10,000 rpm for 15 minutes to remove a precipitate and the resultant supernatant was adjusted to a concentration wherein $A_{280}$ became from 20 to 30. The sample thus obtained was applied to 20 ml of DEAE cellulose column (Whatman $DE_{52}$) equilibrated with a sufficient amount of Tris buffer containing 50 mM NaCl. The column was washed extensively with Tris buffer containing 50 mM NaCl and then eluted with a density gradient of Tris buffer containing 50 mM to 500 mM NaCl at a flow rate of 1.5 ml/min. The eluate was fractionated and the pass-through fractions were concentrated to obtain the desired antibody.

Purified monoclonal antibodies, AF1-52, AF1-81, AF1-113, AF1-114, HaF 1H11, HaF 1E6, HaF 1C10, HaF 2F9, HaF 2E6, HaF 2B7, HaF 1A10, and HaF 1F9 were obtained.

The purity of the monoclonal antibody was determined by using SDS-polyacrylamide gel electrophoresis according to the method of Laemmli, et al.(Nature, 227, 680–685 (1970)).

The sample was treated with ammonium sulfate, and passed through a DEAE cellulose column. The pass-through fraction was reduced with 2-mercaptoethanol and subjected to gel electrophoresis employing 10% polyacrylamide concentration of gel at 180 volts for 2.5 hours.

The results showed that each of the monoclonal antibodies had two bands, a H chain near MW 52K and a L chain near MW 28K.

(6) Determination for Subclass of Antibody

The subclass of antibody was determined by the method below.

The conditioned medium (100 μl) which was obtained from each of the cloned hybridomas was added to wells of 96-well microtiter plates coated with recombinant aFGF as obtained in Reference Example 1, and incubated at room temperature for 2 hours. The conditioned medium was removed, washed, and followed by addition of rabbit anti-mouse antibodies against IgG1, IgG2a, IgG2b, IgG3, K chain, and λ chain (Cappel) in an amount of 100 μl and then incubation at room temperature for 2 hours, respectively.

Each antibody was removed, washed, and followed by addition of HRP-labeled goat anti-rabbit IgG antibody (Cappel) and then incubation at room temperature for 2 hours. The labeled antibody was removed, washed extensively, and followed by enzyme reaction in accordance with the method as described in the above (3). The optical density was measured.

The results show that two monoclonal antibodies, AF1-52 and AF1-81 belong to the subclass IgG2b K type and all of the other 10 monoclonal antibodies belong to the subclass IgG1K type.

(7) Determination for Recognition Site of Antibody

Sites of aFGF which the antibodies recognize were determined by the technique mentioned below.

The antigens, rhaFGF obtained in Reference Example 1, a synthetic peptide residing between positions 1 and 9 of human aFGF (human aFGF (1-9)) and a synthetic peptide residing between positions 133 and 140 of human aFGF (human aFGF (133-140))(obtained in Reference Example 2), a recombinant human basic fibroblast growth factor (rhbFGF) obtained by the method as described in EP No.237,966, and N5 deleted aFGF and N43 deleted aFGF obtained in Reference Example 3 were diluted with 0.0M carbonate buffer (pH 8.5) to a concentration of 10 μg/ml, respectively. The diluted solution (100 μl) was added to wells each of 96-well microtiter plates and allowed to stand at 4° C. overnight to bind each antigen on the solid phase. After each well was washed with 0.0M phosphate buffer (pH 7.0) containing 0.15M NaCl, 200 μl of 0.0M phosphate buffer containing 1% bovine serum albumin (BSA) was distributed thereto, and stored at a chilled place until use.

The conditioned medium (100 μl) from each of 12 clones which were obtained in the above (1) was distributed into the plates as above prepared.

EIA was carried out in the same manner as the method described in the above (3). The results ape shown in Table 9. In Table 9, "−" indicates no antibody binding, "+" indicates antibody binding, and "++" indicates strong antibody binding. The data shown in Table 9 suggest that AF1-52 monoclonal antibody recognizes an epitope laid on an amino acid sequence residing between positions 1 and 9 of aFGF, six monoclonal antibodies, AF1-113, HaF 1H11, HaF 1E6, HaF 1C10, HaF 2F9, and HaF 2B7, recognize an epitope laid on an amino acid sequence residing between positions 6 and 43 of aFGF, and four monoclonal antibodies, AF1-114, HaF 2E6, HaF 1A10, and HaF 1F9, recognize an epitope laid on an amino acid sequence residing between positions 44 and 132 of aFGF.

While AF1-81 monoclonal antibody recognizes whole aFGF, it does not recognize N5 deleted aFGF, and a peptide consisting of an amino acid sequence residing between positions 1 and 9 of aFGF. Consequently, no recognition site of AF1-81 is specified.

TABLE 9

RECOGNITION SITE OF ANTIBODY TO ANTIGEN

| | Monoclonal Antibody | | | | | | | | | | | |
|---|---|---|---|---|---|---|---|---|---|---|---|---|
| | AF1-52 | AF1-81 | AF1-113 | AF1-114 | HaF 1H11 | HaF 1E6 | HaF 1C10 | HaF 2F9 | HaF 2E6 | HaF 2B7 | HaF 1A10 | HaF 1F9 |
| rhaFGF | ++ | + | + | ++ | + | + | + | + | + | + | + | + |
| haFGF(1-9) | ++ | − | − | − | − | − | − | − | − | − | − | − |
| haFGF(133-140) | − | − | − | − | − | − | − | − | − | − | − | − |
| rhbFGF | − | − | − | − | − | − | − | − | − | − | − | − |
| N5 deleted aFGF | − | − | + | ++ | + | + | + | + | + | + | + | + |
| N43 deleted aFGF | − | − | − | + | − | − | − | − | + | − | + | + |

"−" indicates no antibody binding.
"+" indicates antibody binding.
"++" indicates strong antibody binding.

Example 2

(1) Labeling of Antibody with Enzyme

To purified AF1-52 monoclonal antibody (4.2 mg/1.4 ml) was added S-acetylmercaptosuccinic anhydride in a final concentration of 0.4 mg/ml and reacted at room temperature for an hour to introduce SH groups. Tris-HCl buffer (pH 7.0), EDTA and hydroxylamine were added to a concentration of 15 mM, 1.5 mM, and 0.15 mM, respectively, to inactivate unreacted reagents, and subjected to chromatography employing a Sephadex G-25 column to separate SH-introduced antibody fractions.

To 1.4 ml of 0.1M sodium phosphate solution (pH 7.0) containing 10 mg of horseradish peroxidase (HRP) was added N-(γ-maleimidobutyloxy)-succinimide in a concentration of 1.5 mg/ml and reacted at room temperature for an hour to introduce maleimido groups. Maleimidated HRP was isolated by chromatography employing a Sephadex G-25 column.

The maleimidated HRP was mixed with the SH-introduced antibody and coupled at 4° C. overnight. After coupling reaction, HRP-labeled AF1-52 antibody was isolated by chromatography employing a Ultro-gel AcA44 column.

(2) Preparation of Antibody Bound Solid Phase

The purified antibodies, AF1-81, AF1-114, and HaF 1C10, were diluted with 0.01M carbonate buffer (pH 8.5) to a concentration of 10 μg/ml, respectively. The solution of one antibody or a mixture of three antibodies (100 μl each) was distributed to wells each of 96-well microtiter plates and allowed to stand at 4° C. overnight to bind antibodies on the solid phase. After each well was washed with 0.0M phosphate buffer (pH 7.0) containing 0.15M NaCl, 200 μl of 0.0M phosphate buffer containing 1% BSA was distributed thereto, and stored at a chilled place until use.

(3) Sandwich (two-site) EIA

To the wells bound with antibodies was added 100 μl each of rhaFGF solutions which were prepared to various concentrations and incubated at 4° C. overnight. After removal of the aFGF solution, 100 μl of 200-fold diluted HRP-labeled AF1-52 antibody was added to each well and incubated at room temperature for two hours. After the labeled antibody was removed, a HRP substrate solution was added thereto. The enzyme reaction was carried out in the manner as the method described in Example 1 and the absorbance at 492 nm was measured.

The results show that the mixed use of three monoclonal antibodies, AF1-81, AF1-114, and HaF 1C10, achieves higher sensitivities than any of sole use thereof. The detection limit of aFGF is 1.5 pg/well. This indicates that a very low concentration is detectable (FIG. 10).

Figure 10:
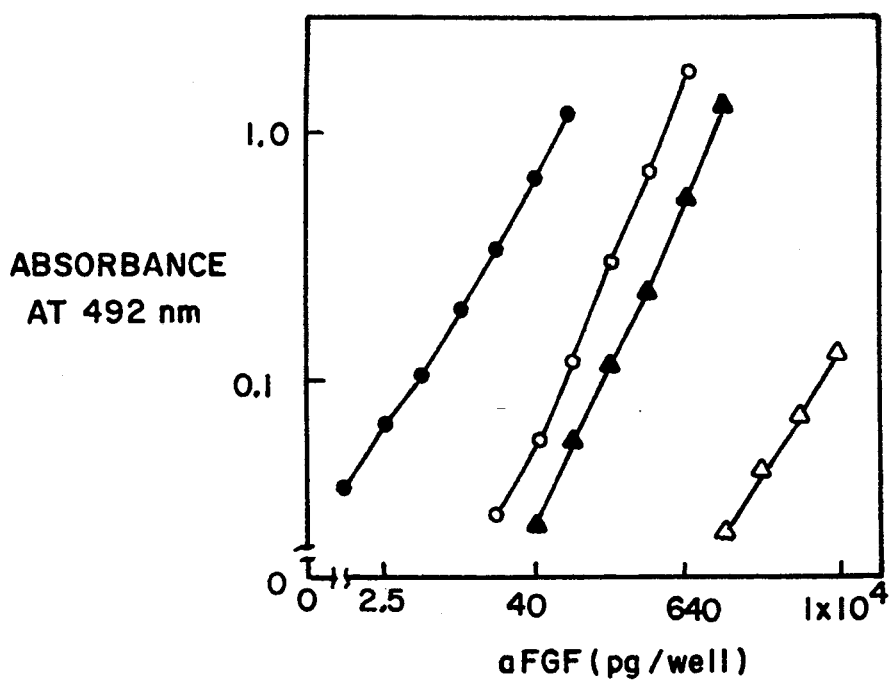
FIG. 10 shows the results of detection sensitivity in sandwich EIA of aFGF, obtained in Example 5(3).

In FIG. 10, △ denotes the results of monoclonal antibody, AF1-81, ▲ denotes the results of monoclonal antibody, AF1-114, ○ denotes the results of monoclonal antibody, HaF 1C10, and ● denotes the results of the mixture of three antibodies.

Figure 11:
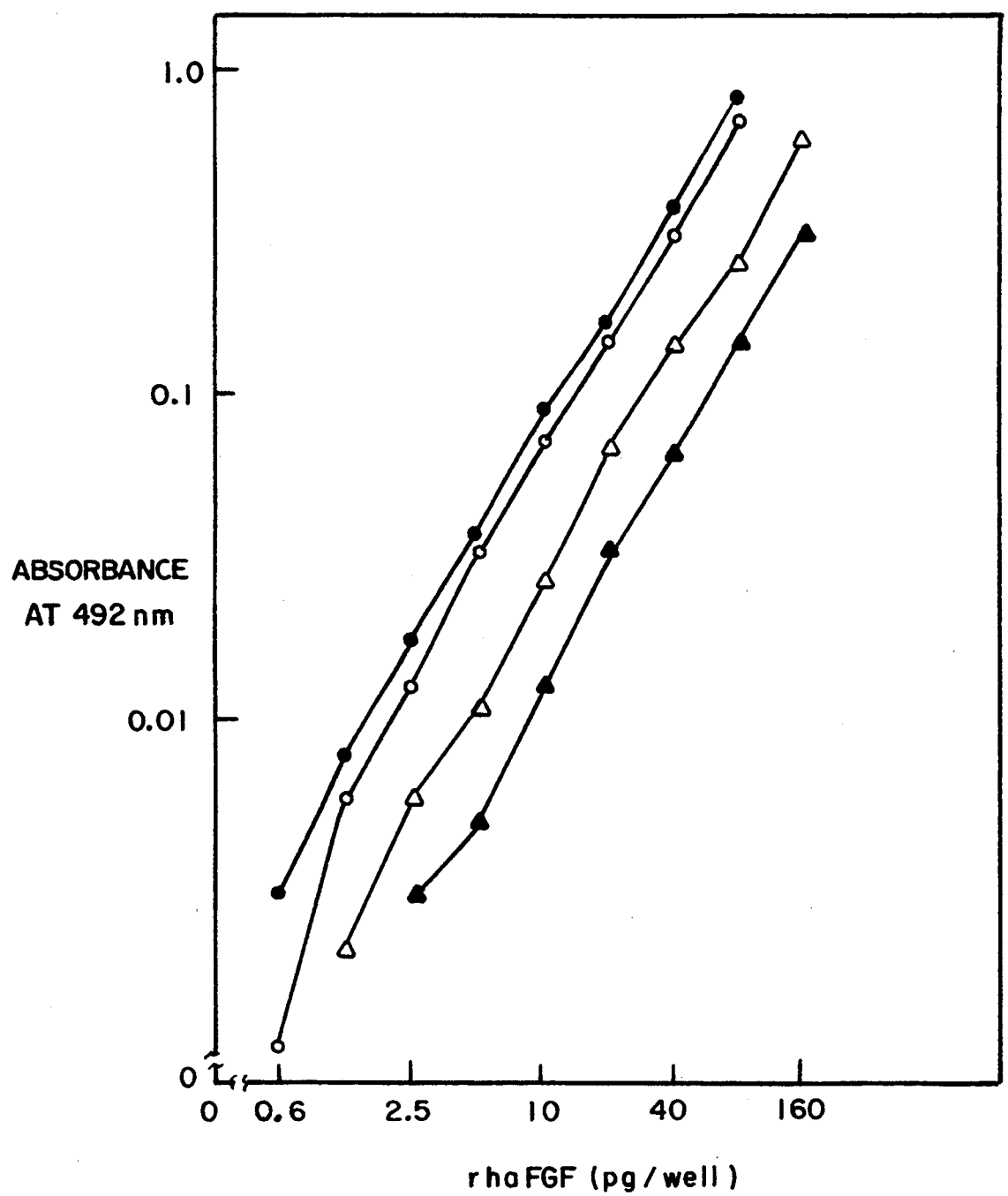
FIG. 11 shows the results of detection sensitivity in sandwich EIA of aFGF, obtained in Example 5(3).

The mixed use of the three monoclonal antibodies achieves more sensitivities for the detection of aFGF when compared with the mixed use of any two of the antibodies (FIG. 11).

In FIG. 11, ▲ denotes the results of the mixture of two monoclonal antibodies, AF1-81 and AF1-114, △ denotes the results of the mixture of two monoclonal antibodies, HaF 1C10 and AF1-81, ○ denotes the results of the mixture of two monoclonal antibodies, HaF 1C10 and AF1-114, and ● denotes the results of the mixture of three antibodies, AF1-81, AF1-114, and HaF 1C10.

(4) Specificity of Sandwich EIA

In order to determine whether the established sandwich EIA is specific for aFGF, the assay was conducted using various concentrations of rhbFGF as an antigen.

Figure 12:
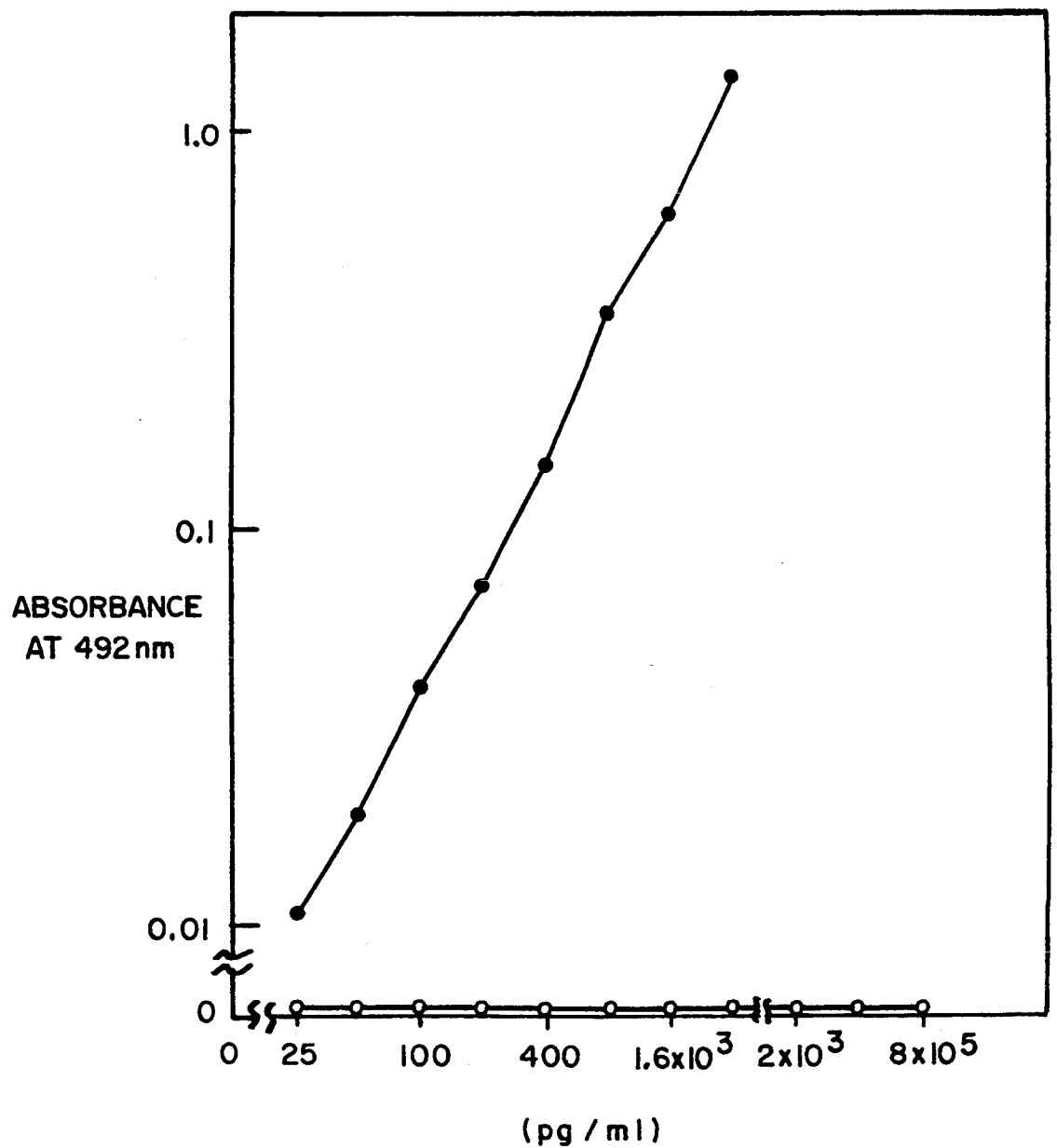
FIG. 12 shows the results of specificity in sandwich EIA of aFGF, obtained in Example 5(4).

To wells coupled with the mixture of three antibodies was added 100 μl of the above-mentioned antigen preparation (Example 2(3)) and incubated at 4° C. overnight. After removal of the antigen, 100 μl of 200-fold diluted HRP-labeled AF1-52 antibody was added to each well and examined for the presence of reactivity in the same manner as above. In this sandwich EIA, the aFGF binding to monoclonal antibodies was shown to be immunospecific because rhbFGF was not detected even in a high concentration of 800 ng/ml (FIG. 12). In FIG. 12, ● denotes the results of aFGF and ▬ denotes the results of bFGF.

(5) Effect of Heparin

The assay was examined for the influence of heparin on the aFGF binding to four monoclonal antibodies (AF1-52, AF1-81, AF1-114, and HaF 1C10).

To aFGF bound wells prepared by the method as described in Example 1 was added each of the above antibodies in the presence of heparin and the change of antibody binding was assayed. The results are shown in Table 10.

TABLE 10

| Influence of Heparin on Binding of Antibody to aFGF | | | |
|---|---|---|---|
| | Heparin (μg/ml) | | |
| Monoclonal antibody | 0 | 10 | 100 |
| AF1-52 | 0.961 | 0.834 | 0.887 |
| AF1-81 | 0.278 | 0.278 | 0.224 |
| AF1-114 | 1.498 | 1.478 | 1.398 |
| HaF 1C10 | 0.964 | 1.008 | 0.944 |

It is clear from Table 10 that even in the presence of heparin with concentrations of 10 μl and 100 μg/ml, none of monoclonal antibody bindings to aFGF is inhibited and none of the antibodies recognizes heparin-binding sites of aFGF.

The EIA sandwich was also examined for the influence of heparin. To various concentrations of aFGF solution was added heparin to give 10 μg/ml or 100 μg/ml and used in the sandwich EIA. The results show that the antibody binding to aFGF in this EIA was inhibited very little even in the presence of heparin and the detection sensitivity was up to 2 pg/well. This indicates that the EIA according to the present invention was highly sensitive (FIG. 13).

Figure 13:
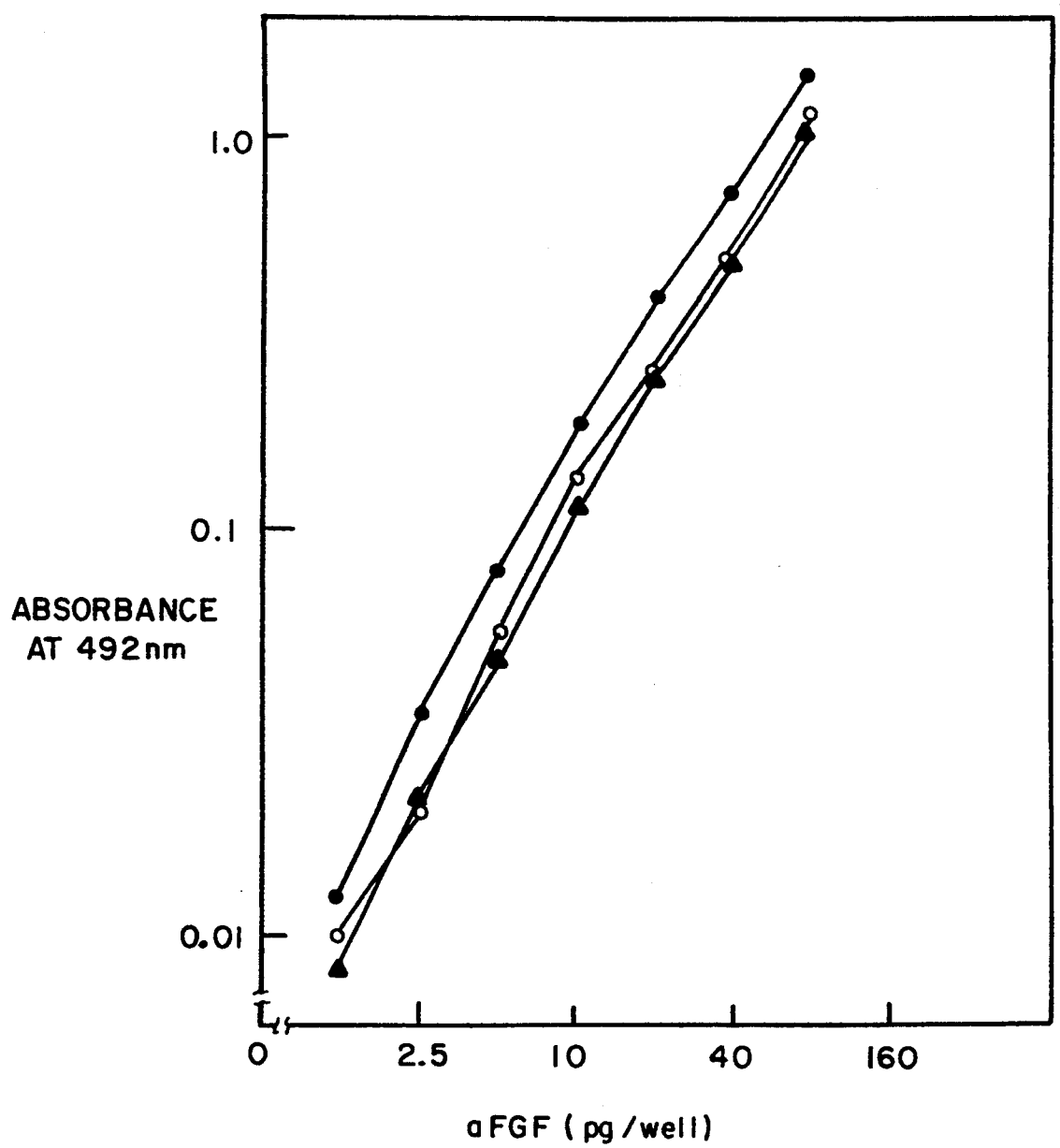
FIG. 13 shows the results of influence of heparin on sandwich EIA of aFGF, obtained in Example 5(5).

In FIG. 13, ● denotes the results of the absence of heparin, ○ denotes the results of the presence of heparin in a concentration of 100 μg/ml, and ▲ denotes the results of the presence of heparin in a concentration of 10 μg/ml. Accordingly, the monoclonal antibodies according to the present invention bind specifically to aFGF and further exhibit high avidity; therefore they are useful as reagents for assay of aFGF, etc.

Example 3

(1) Preparation of Resin Coupled with Antibody

CNBr-activated Sepharose 4B (1 g) is repeated by washing and swelling with 200 ml of 1M hydrochloric acid on a glass filter. The gel is washed with a coupling buffer (0.1M carbonate buffer (pH 8.0) containing 0.5M NaCl). Then the gel is added to a coupling buffer containing 2 mg each of monoclonal antibodies, AF1-81, HaF 1C10 and AF1-114, which are obtained in Example 1 (5), and followed by the addition of a coupling buffer to a total volume of 10 ml. The mixture is stirred at 4° C. for 20 hours. The gel is recovered by filtration on a glass filter, transferred into 0.2M Gly-NaOH (pH 8.0) and stirred at room temperature for 2 hours. The gel is recovered by filtration, washed with 0.1M acetate buffer (pH 8.0) containing a coupling buffer and 0.5M NaCl and stored in 0.02M phosphate buffer (pH 7.0) at 4° C.

(2) Purification of Human aFGF

The gel (0.5 ml) prepared in the above (1) is packed into a column (inner diameter: 0.8 cm) and washed extensively with a buffer A (0.05M HEPES buffer (pH 7.5) containing 0.15M NaCl).

E. coli MM294 (DE3)/pLys S, pTB975 obtained in Reference Example 3(b) is cultured. The microorganisms collected from 5 ml of the culture are suspended into 1 ml of ice-cooled 10 mM Tris-HCl (pH 7.4) containing 10 mM EDTA, 0.2M NaCl, 10% sucrose and 0.25 mM phenylmethylsulfonyl fluoride (PMSF). To the suspension is added egg white lysozyme to 0.5 mg/ml. The mixture is allowed to stand in an ice bath for an hour, followed by incubation at 37° C. for 5 min., sonicated under ice cooling, and centrifuged (SORVALL, 18K rpm, 30 min., 4° C.) to give a supernatant. The supernatant (50 μl) is subjected to the above column which is washed extensively with a buffer A and eluted with a buffer B (0.2M glycine-hydrochloric acid buffer (pH 2.0)) to yield an eluate containing aFGF. The eluate is neutralized with 1M Tris.

By examining a biological activity for human aFGF according to the method of Sasada, et al. as described in Reference Example 1 (e), the eluate shows a specific activity equivalent to that of aFGF obtained in Reference Example 1 (e).

It is understood that the preceding representative examples may be varied within the scope of the present invention by one skilled in the art to achieve essentially the same results.

As many widely different embodiments of this invention may be made without departing from the spirit and scope thereof, it is to be understood that this invention is not limited to the specific embodiments thereof except as defined in the appended claims.

The following references, which are referred to for their disclosures at various points in this application, are incorporated herein by reference.

1. D. Gospodarowicz et al.; Endocrine Reviews, 8: 95 (1987).
2. G. Gimenez-Gallego, et al., Science, 230: 1385 (1985).
3. F. Esch, et al., Biochemical and Biophysical Research Communications, Vol. 133: 544 (1985).
4. G. Gimenez-Gallego, et al., Biochemical and Biophysical Research Communications, Vol.138, No. 2, pp. 611–617, (1986).
5. EP No. 0 319 052.
6. Lather, R. F. and Lecoq, J. P., Genetic Engineering, Academic Press, (1983), 31–50.
7. Smith, M. and Gillam, S., Genetic Engineering; Principle and Method, Plenum Press, (1981), Vol.3, 1–32.
8. Ichimori et al.: Journal of Immunological Methods, 80, 55 (1985).
9. Köhler and Milstein, Nature, 256, 495 (1975).
10. Moore, G. E., et. al., Journal of American Medical Association, 199, 549 (1967).
11. Taisha ( Japan ), Vol.8, (1971) 696.
12. EP No. 237,966.
13. Biotechnology, 5, 960 (1987).
14. Journal of Biological Chemistry, 263, 16471 (1988).
15. ICSU Short Reports Volume 8, Advances in Gene Technology: Protein Engineering and Production, Proceedings of the 1988 Miami Bio/Technology Winter Symposium, IRL Press, page 110.
16. Methods in Enzymology, 101, 20–78 (1983).
17. Studier, F. W. et al., J. Mol. Biol., 189, 113–130 (1986).
18. Gene, 56, 125–135 (1987).
19. Sasada, et al., Mol. Cell Biol., 8, 588–594 (1988).
20. Staehelin, et al., Journal of Biological Chemistry, 256, 9750–9754 (1981).
21. Laemmli, et al., Nature, 227, 680–685 (1970).

What is claimed is:

1. A monoclonal antibody which recognizes a human acidic fibroblast growth factor (aFGF) protein and has the following characteristics:
    (a) molecular weight; about 140000 to about 160000,
    (b) non-cross reactive with basic fibroblast growth factor,
    (c) belonging to the immunoglobulin class IgG; and
    (d) the binding affinity of said antibody is not significantly inhibited by heparin wherein said antibody is selected from the group consisting of AF1-52, AF1-81, AF1-114 and HaF 1C10.

2. A cloned hybridoma selected from the group consisting of the following hybrid cell lines (their accession number): AF1-52 (FERM BP-2607), AF1-81 (FERM BP-2681), AF1-114 (FERM BP-2608), and HaF 1C10 (FERM BP 2605).

* * * * *